(12) United States Patent
von Moltke et al.

(10) Patent No.: US 12,251,381 B2
(45) Date of Patent: *Mar. 18, 2025

(54) ARIPIPRAZOLE DOSING STRATEGY

(71) Applicant: Alkermes Pharma Ireland Limited, Dublin (IE)

(72) Inventors: Lisa L. von Moltke, Newton, MA (US); Peter J. Weiden, Newton, MA (US); Marjie L. Hard, Lexington, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 33 days.

This patent is subject to a terminal disclaimer.

(21) Appl. No.: 17/665,015

(22) Filed: Feb. 4, 2022

(65) Prior Publication Data

US 2022/0152021 A1    May 19, 2022

Related U.S. Application Data

(63) Continuation of application No. 16/291,768, filed on Mar. 4, 2019, now Pat. No. 11,273,158.

(60) Provisional application No. 62/638,587, filed on Mar. 5, 2018.

(51) Int. Cl.
| | |
|---|---|
| *A61K 31/497* | (2006.01) |
| *A61K 9/00* | (2006.01) |
| *A61K 31/496* | (2006.01) |
| *A61K 47/02* | (2006.01) |
| *A61K 47/12* | (2006.01) |
| *A61K 47/26* | (2006.01) |
| *A61P 25/18* | (2006.01) |

(52) U.S. Cl.
CPC .......... *A61K 31/497* (2013.01); *A61K 31/496* (2013.01); *A61K 47/02* (2013.01); *A61K 47/12* (2013.01); *A61K 47/26* (2013.01); *A61P 25/18* (2018.01); *A61K 9/0019* (2013.01); *A61K 9/0053* (2013.01)

(58) Field of Classification Search
CPC .... A61K 31/496; A61K 31/497; A61K 47/02; A61K 47/12; A61K 47/26; A61P 25/18
See application file for complete search history.

(56) References Cited

U.S. PATENT DOCUMENTS

| | | |
|---|---|---|
| 2,418,499 A | 4/1947 | James |
| 3,266,984 A | 8/1966 | Ueda et al. |
| 3,523,121 A | 8/1970 | Lewis et al. |
| 3,573,308 A | 3/1971 | Ning et al. |
| 3,798,219 A | 3/1974 | Strandtmann et al. |
| 3,957,808 A | 5/1976 | Miller et al. |
| 1,160,099 A | 7/1979 | Bodor |
| 4,204,065 A | 5/1980 | Bodor |
| 4,234,584 A | 11/1980 | Lattrell et al. |
| 4,260,769 A | 4/1981 | Stella et al. |
| 4,267,326 A | 5/1981 | Ozaki et al. |
| 4,428,935 A | 1/1984 | Myers |
| 4,443,464 A | 4/1984 | Biedermann et al. |
| 4,448,906 A | 5/1984 | Deinet et al. |
| 4,500,708 A | 2/1985 | Chorvat et al. |
| 4,594,190 A | 6/1986 | Giani et al. |
| 4,694,006 A | 9/1987 | Bundgaard et al. |
| 4,727,151 A | 2/1988 | Bodor |
| 4,734,416 A | 3/1988 | Banno et al. |
| 4,760,057 A | 7/1988 | Alexander |
| 4,831,031 A | 5/1989 | Lowe, III et al. |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,229,382 A | 7/1993 | Chakrabarti et al. |
| 5,236,927 A | 8/1993 | Jones et al. |
| 5,350,747 A | 9/1994 | Howard |
| 5,462,934 A | 10/1995 | Goto et al. |
| 5,510,118 A | 4/1996 | Bosch et al. |
| 5,532,372 A | 7/1996 | Saji et al. |
| 5,612,346 A | 3/1997 | Mesens et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,945,416 A | 8/1999 | Shannon et al. |
| 5,985,856 A | 11/1999 | Stella et al. |
| 6,127,357 A | 10/2000 | Cliffe et al. |
| 6,133,248 A | 10/2000 | Stella |
| 6,150,366 A | 11/2000 | Arenson et al. |
| 6,169,084 B1 | 1/2001 | Bunnell et al. |

(Continued)

FOREIGN PATENT DOCUMENTS

| | | |
|---|---|---|
| CA | 1157677 A | 11/1983 |
| CN | 102260290 A | 11/2011 |

(Continued)

OTHER PUBLICATIONS

Hard (CNS Drugs vol. 31 pp. 617-624 published online Jun. 8, 2017). (Year: 2017).*
Anonymous. Alkermes Unveils Investigational Product Designed for Initiation Onto ARISTADA® for Treatment of Schizophrenia, Business Wire, Oct. 26, 2017.
Hard et al., "Population Pharmacokinetic Analysis and Model-Based Simulations of Aripiprazole for a 1-Day Initiation Regimen for the Long-Acting Antipsychotic Aripiprazole Lauroxil", European Journal of Drug Metabolism and Pharmacokinetics, vol. 43. No. 4, Jun. 11, 2018, pp. 461-469.
Hard et al., "Pharmacokinetic Evaluation of a 1-Day Treatment Initiation Option for Starting Long-Acting Aripiprazole Lauroxil for Schizophrenia", Journal of Clinical Psychopharmacology, vol. 38, No. 5. Oct. 1, 2018. pp. 435-441.

(Continued)

*Primary Examiner* — Theodore R. Howell
*Assistant Examiner* — George W Kosturko
(74) *Attorney, Agent, or Firm* — Lathrop GPM LLP; Brian C. Trinque; Nicole Sassu

(57) ABSTRACT

The present invention relates to methods of treating schizophrenia using a combination of aripiprazole, aripiprazole lauroxil, and a nanoparticle dispersion of aripiprazole lauroxil.

27 Claims, 9 Drawing Sheets

(56) References Cited

U.S. PATENT DOCUMENTS

| | | |
|---|---|---|
| 6,180,095 B1 | 1/2001 | Greenwald et al. |
| 6,444,668 B1 | 9/2002 | Grubb et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 6,977,257 B2 | 12/2005 | Parab et al. |
| 7,053,092 B2 | 5/2006 | Jordon et al. |
| 7,112,603 B2 | 9/2006 | Moon et al. |
| 7,115,587 B2 | 10/2006 | Nerurkar et al. |
| 7,160,888 B2 | 1/2007 | Johnson et al. |
| 7,374,779 B2 | 5/2008 | Chen et al. |
| 7,538,121 B2 | 5/2009 | MacDonald et al. |
| 7,550,445 B2 | 6/2009 | Nerurkar et al. |
| 7,807,680 B2 | 10/2010 | Kostanski et al. |
| 7,910,577 B2 | 3/2011 | Liversidge et al. |
| 7,981,906 B2 | 7/2011 | Dull et al. |
| 8,017,515 B2 | 9/2011 | Marimuthu et al. |
| 8,017,615 B2 | 9/2011 | Bando et al. |
| 8,030,313 B2 | 10/2011 | Kostanski et al. |
| 8,247,420 B2 | 8/2012 | Bhat et al. |
| 8,338,427 B2 | 12/2012 | Brown |
| 8,338,428 B2 | 12/2012 | Brown |
| 8,399,469 B2 | 3/2013 | Bando et al. |
| 8,431,576 B2 | 4/2013 | Remenar et al. |
| 8,518,421 B2 | 8/2013 | Kothari et al. |
| 8,536,328 B2 | 9/2013 | Remenar et al. |
| 8,580,796 B2 | 11/2013 | Bando et al. |
| 8,592,427 B2 | 11/2013 | Blumberg et al. |
| 8,642,600 B2 | 2/2014 | Jordan et al. |
| 8,642,760 B2 | 2/2014 | Bando et al. |
| 8,669,281 B1 | 3/2014 | Zeidan et al. |
| 8,686,009 B2 | 4/2014 | Blumberg et al. |
| 8,796,276 B2 | 8/2014 | Remenar et al. |
| 9,034,867 B2 | 5/2015 | Perry et al. |
| 9,072,788 B2 | 7/2015 | Blumberg et al. |
| 9,102,618 B2 | 8/2015 | Blumberg et al. |
| 9,193,685 B2 | 11/2015 | Perry et al. |
| 9,351,976 B2 | 5/2016 | Perry et al. |
| 9,452,131 B2 | 9/2016 | Hickey et al. |
| 9,526,726 B2 | 12/2016 | Hickey et al. |
| 9,585,965 B2 | 3/2017 | Blumberg et al. |
| 9,650,341 B2 | 5/2017 | Remenar et al. |
| 9,861,699 B2 | 1/2018 | Perry et al. |
| 9,993,556 B2 | 6/2018 | Perry et al. |
| 9,999,670 B2 | 6/2018 | Perry et al. |
| 10,004,807 B2 | 6/2018 | Perry et al. |
| 10,023,537 B2 | 7/2018 | Remenar et al. |
| 10,040,787 B2 | 8/2018 | Blumberg et al. |
| 10,064,859 B2 | 9/2018 | Morales, Jr. et al. |
| 10,085,980 B2 | 10/2018 | Hickey et al. |
| 10,112,903 B2 | 10/2018 | Remenar et al. |
| 10,238,651 B2 | 3/2019 | Hickey et al. |
| 11,273,158 B2 * | 3/2022 | von Moltke et al. ... A61P 25/18 |
| 2002/0146455 A1 | 10/2002 | Kundu et al. |
| 2002/0176841 A1 | 11/2002 | Barker et al. |
| 2003/0064998 A1 | 4/2003 | Francois et al. |
| 2003/0077297 A1 | 4/2003 | Chen et al. |
| 2004/0077594 A1 | 4/2004 | Nerurkar et al. |
| 2004/0101557 A1 | 5/2004 | Gibson et al. |
| 2004/0138230 A1 | 7/2004 | Andreana et al. |
| 2004/0254182 A1 | 12/2004 | Mulvihill et al. |
| 2005/0019436 A1 | 1/2005 | Burch et al. |
| 2005/0032811 A1 | 2/2005 | Brown |
| 2005/0079185 A1 | 4/2005 | Parisot et al. |
| 2005/0203089 A1 | 9/2005 | Starrett et al. |
| 2005/0282821 A1 | 12/2005 | Lesur et al. |
| 2006/0040922 A1 | 2/2006 | Greco et al. |
| 2006/0040932 A1 | 2/2006 | Eijgendaal et al. |
| 2006/0142333 A1 | 6/2006 | MacDonald et al. |
| 2006/0154918 A1 | 7/2006 | Liversidge et al. |
| 2006/0194345 A1 | 8/2006 | Uchiyama et al. |
| 2006/0293217 A1 | 12/2006 | Barker et al. |
| 2007/0031513 A1 | 2/2007 | Kikuchi et al. |
| 2007/0148100 A1 | 6/2007 | Jenkins |
| 2007/0191611 A1 | 8/2007 | Rao et al. |
| 2007/0213300 A1 | 9/2007 | Liu et al. |
| 2008/0085888 A1 | 4/2008 | Breining et al. |
| 2008/0143403 A1 | 6/2008 | Huang et al. |
| 2008/0186971 A1 | 8/2008 | Carmichael et al. |
| 2008/0233053 A1 | 9/2008 | Gross et al. |
| 2008/0261954 A1 | 10/2008 | Maelicke |
| 2008/0312199 A1 | 12/2008 | Glinsky |
| 2008/0318905 A1 | 12/2008 | Muhammad et al. |
| 2009/0053329 A1 | 2/2009 | Peters et al. |
| 2009/0068290 A1 | 3/2009 | Bourin et al. |
| 2009/0069419 A1 | 3/2009 | Jandeleit et al. |
| 2009/0118242 A1 | 5/2009 | Burch et al. |
| 2009/0143403 A1 | 6/2009 | Brown |
| 2009/0163519 A1 | 6/2009 | Vermeulen et al. |
| 2009/0163545 A1 | 6/2009 | Goldfarb |
| 2009/0169632 A1 | 7/2009 | Lu et al. |
| 2009/0311347 A1 | 12/2009 | Oronsky et al. |
| 2010/0098641 A1 | 4/2010 | Baker et al. |
| 2010/0197641 A1 | 8/2010 | Mazess et al. |
| 2010/0203129 A1 | 8/2010 | Andersen et al. |
| 2010/0286136 A1 | 11/2010 | Jones et al. |
| 2010/0292316 A1 | 11/2010 | Sanders et al. |
| 2010/0293129 A1 | 11/2010 | Dong et al. |
| 2010/0331356 A1 | 12/2010 | Legen et al. |
| 2011/0003823 A1 | 1/2011 | Horn |
| 2011/0003828 A1 | 1/2011 | Blumberg et al. |
| 2011/0015156 A1 | 1/2011 | Zeidan et al. |
| 2011/0105536 A1 | 5/2011 | Lewyn-Briscoe et al. |
| 2011/0166128 A1 | 7/2011 | Remenar et al. |
| 2011/0166156 A1 | 7/2011 | Blumberg et al. |
| 2011/0166194 A1 | 7/2011 | Blumberg et al. |
| 2011/0178068 A1 | 7/2011 | Almarsson et al. |
| 2011/0195095 A1 | 8/2011 | Liversidge et al. |
| 2011/0236478 A1 | 9/2011 | Dokou et al. |
| 2011/0275803 A1 | 11/2011 | Remenar et al. |
| 2011/0319422 A1 | 12/2011 | Blumberg et al. |
| 2012/0004165 A1 | 1/2012 | Keil et al. |
| 2012/0015866 A1 | 1/2012 | Blumberg et al. |
| 2012/0202823 A1 | 8/2012 | Zeidan et al. |
| 2012/0238552 A1 * | 9/2012 | Perry ............... A61P 25/24 514/220 |
| 2012/0316180 A1 | 12/2012 | Bando et al. |
| 2013/0003046 A1 | 1/2013 | Izawa et al. |
| 2013/0096089 A1 | 4/2013 | Remenar et al. |
| 2013/0184265 A1 | 7/2013 | Blumberg et al. |
| 2013/0267503 A1 | 10/2013 | Perry et al. |
| 2013/0267504 A1 | 10/2013 | Perry et al. |
| 2013/0267505 A1 | 10/2013 | Perry et al. |
| 2014/0051853 A1 | 2/2014 | Bürger et al. |
| 2014/0088115 A1 | 3/2014 | Perry et al. |
| 2014/0094472 A1 | 4/2014 | Blumberg et al. |
| 2014/0221653 A1 | 8/2014 | Blumberg et al. |
| 2014/0275048 A1 | 9/2014 | Zeidan et al. |
| 2014/0350254 A1 | 11/2014 | Remenar et al. |
| 2015/0087654 A1 | 3/2015 | Raoufinia |
| 2015/0258115 A1 | 9/2015 | Perry et al. |
| 2015/0265529 A1 | 9/2015 | Hickey et al. |
| 2015/0274670 A1 | 10/2015 | Remenar et al. |
| 2015/0376143 A1 | 12/2015 | Blumberg et al. |
| 2016/0038508 A1 | 2/2016 | Perry et al. |
| 2016/0045495 A1 * | 2/2016 | Cresswell et al. ... A61K 31/496 514/253.07 |
| 2016/0136279 A1 | 5/2016 | Perry et al. |
| 2016/0263111 A1 | 9/2016 | Hickey et al. |
| 2017/0015659 A1 | 1/2017 | Blumberg et al. |
| 2018/0369239 A1 | 12/2018 | Hickey et al. |
| 2019/0031648 A1 | 1/2019 | Blumberg et al. |
| 2019/0084937 A1 | 3/2019 | Remenar et al. |

FOREIGN PATENT DOCUMENTS

| | | |
|---|---|---|
| DE | 1070760 B | 12/1959 |
| DE | 11273533 B | 7/1968 |
| DE | 4439493 A1 | 5/1996 |
| EP | 0 207 581 A2 | 1/1987 |
| EP | 0 281 309 A1 | 9/1988 |
| EP | 0 339 976 A1 | 11/1989 |
| EP | 0 367 141 A2 | 5/1990 |
| EP | 0 409 435 A1 | 1/1991 |

(56) References Cited

FOREIGN PATENT DOCUMENTS

| | | |
|---|---|---|
| EP | 0 590 793 A1 | 4/1994 |
| EP | 0 925 061 A1 | 6/1999 |
| EP | 1 891 956 A1 | 2/2008 |
| GB | 849541 A | 9/1960 |
| GB | 2017701 A | 10/1979 |
| GB | 2054371 A | 2/1981 |
| JP | S60-2331 A | 1/1985 |
| JP | S61-171467 A | 8/1986 |
| JP | S61-267580 A | 11/1986 |
| JP | S62-061979 A | 4/1987 |
| JP | S63-284165 A | 11/1988 |
| JP | S63-301861 A | 12/1988 |
| JP | H02-191256 A | 7/1990 |
| JP | H05-194517 A | 8/1993 |
| JP | H08-281115 A | 10/1996 |
| WO | 1990/08128 A1 | 7/1990 |
| WO | 1990/14080 A1 | 11/1990 |
| WO | 1991/00863 A1 | 1/1991 |
| WO | 1991/15488 A1 | 10/1991 |
| WO | 1992/06089 A1 | 4/1992 |
| WO | 1993/25197 A1 | 12/1993 |
| WO | 1996/12725 A1 | 5/1996 |
| WO | 1996/26929 A1 | 9/1996 |
| WO | 1997/36893 A1 | 10/1997 |
| WO | 1997/41132 A1 | 11/1997 |
| WO | 1997/43284 A1 | 11/1997 |
| WO | 1998/49157 A1 | 11/1998 |
| WO | 1999/33846 A2 | 7/1999 |
| WO | 2000/50417 A1 | 8/2000 |
| WO | 2000/66571 A1 | 11/2000 |
| WO | 2001/90103 A2 | 11/2001 |
| WO | 2002/49573 A2 | 6/2002 |
| WO | 2002/096351 A2 | 12/2002 |
| WO | 2002/100861 A1 | 12/2002 |
| WO | 2003/080047 A1 | 10/2003 |
| WO | 2003/084572 A1 | 10/2003 |
| WO | 2004/012671 A2 | 2/2004 |
| WO | 2004/026864 A1 | 4/2004 |
| WO | 2004/029054 A1 | 4/2004 |
| WO | 2004/037819 A1 | 5/2004 |
| WO | 2004/067546 A1 | 8/2004 |
| WO | 2004/089925 A1 | 10/2004 |
| WO | 2005/016262 A2 | 2/2005 |
| WO | 2005/019215 A1 | 3/2005 |
| WO | 2005/066165 A1 | 7/2005 |
| WO | 2005/079807 A1 | 9/2005 |
| WO | 2005/090357 A1 | 9/2005 |
| WO | 2005/120577 A2 | 12/2005 |
| WO | 2006/037090 A2 | 4/2006 |
| WO | 2006/055603 A2 | 5/2006 |
| WO | 2006/085219 A2 | 8/2006 |
| WO | 2006/090273 A2 | 8/2006 |
| WO | 2007/018943 A2 | 2/2007 |
| WO | 2007/052104 A2 | 5/2007 |
| WO | 2007/059111 A2 | 5/2007 |
| WO | 2007/082907 A1 | 7/2007 |
| WO | 2007/084391 A2 | 7/2007 |
| WO | 2008/025781 A1 | 3/2008 |
| WO | 2008/124030 A1 | 10/2008 |
| WO | 2009/003136 A1 | 12/2008 |
| WO | 2009/037172 A1 | 3/2009 |
| WO | 2009/052467 A1 | 4/2009 |
| WO | 2009/060473 A2 | 5/2009 |
| WO | 2010/085684 A1 | 7/2010 |
| WO | 2010/135703 A2 | 11/2010 |
| WO | 2010/149755 A1 | 12/2010 |
| WO | 2010/151689 A1 | 12/2010 |
| WO | 2010/151711 A1 | 12/2010 |
| WO | 2011/084846 A1 | 7/2011 |
| WO | 2011/084848 A2 | 7/2011 |
| WO | 2011/160084 A1 | 12/2011 |
| WO | 2011/161030 A1 | 12/2011 |
| WO | 2012/129156 A1 | 9/2012 |
| WO | 2013/142198 A1 | 9/2013 |
| WO | 2013/142202 A1 | 9/2013 |
| WO | 2013/142205 A1 | 9/2013 |
| WO | 2014/080285 A2 | 5/2014 |
| WO | 2015/143145 A1 | 9/2015 |

OTHER PUBLICATIONS

Hard et al., "Aripiprazole Lauroxii: Pharmacokinetic Profile of This Long-Acting Injectable Antipsychotic in Persons with Schizophrenia", Journal of Clinical Psychopharmacology, vol. 37, No. 3. Jun. 1, 2017.

Walling et al., "F197. Aripiprazole Lauroxil NanoCrystal Dispersion: A Potential 1-Day Initiation regimen for Long-Acting Aripiprazole Lauroxil", Biological Psychiatry, vol. 83, No. 9, Apr. 9, 2018.

Meyer et al., "27 A New Method for Initiating Treatment with the Long-acting Antipsychotic Aripiprazole Lauroxil", CNS spectrums, Feb. 1, 2019. pp. 188-189.

Wu Jun-Yi et al., Model-informed Approaches for Alternative Aripiprazole Dosing Regimens and Missed Dose management: Towards Better Adherence to Antipsychotic Pharmacotherapy, European Journal of Drug Metabolism and Pharmacokinetics, (2018) 43:471-473.

International Search Report and Written Opinion in related PCT Application No. PCT/US2019/020578, mailed Jul. 4, 2019 (16 pages).

(Feb. 1, 2008) "CAS RN 1001254-47-2".

(Jul. 31, 2002) "CAS RN 441314-50-7".

(Nov. 16, 1984) "CAS RN 52598-34-2".

(Nov. 16, 1984) "CAS RN 66395-34-4".

(Oct. 11, 2004) "CAS RN 760152-91-8".

(Nov. 16, 1984) "CAS RN 91305-39-4".

(Oct. 6, 2015) "FDA Approves New Injectable Drug to Treat Schizophrenia", FDA news release.

International Preliminary Report on Patentability received for PCT Patent Application No. PCT/US2012/029625, mailed on Oct. 3, 2013, 12 Pages.

International Search Report and Written Opinion received for PCT Patent Application No. PCT/ US2015/046525, mailed on Nov. 30, 2015, 7 Pages.

International Search Report and Written Opinion received for PCT Patent Application No. PCT/IB2013/002995, mailed on Jun. 18, 2014, 7 Pages.

International Search Report and Written Opinion received for PCT Patent Application No. PCT/US2010/039855, mailed on Aug. 23, 2010, 11 Pages.

International Search Report and Written Opinion received for PCT Patent Application No. PCT/US2012/029625, mailed on Aug. 28, 2012, 8 Pages.

International Search Report and Written Opinion received for PCT Patent Application No. PCT/US2013/030905, mailed on Jun. 17, 2013, 11 Pages.

International Search Report and Written Opinion received for PCT Patent Application No. PCT/US2013/030933, mailed on Jun. 26, 2013, 14 Pages.

International Search Report and Written Opinion received for PCT Patent Application No. PCT/US2013/030945, mailed on Jun. 27, 2013, 17 Pages.

International Search Report and Written Opinion received for PCT Patent Application No. PCT/US2013/060677, mailed on Feb. 20, 2014, 6 Pages.

International Search Report and Written Opinion received for PCT Patent Application No. PCT/US2015/021448, mailed on Jun. 19, 2015, 12 Pages.

International Search Report received for PCT Patent Application No. PCT/US2013/030916, mailed on Aug. 27, 2013, 18 Pages.

(1995) "Medication Administration Techniques: Injections", Pearson Education, Inc.

(1984) "The HLB System: a time-saving guide to emulsifier selection", Chapter 5, ICI Americas Inc. Wilmington, 4 Pages.

Abilify Maintena® "Prescribing Information Leaflet".

Akers, et al. (May-Jun. 1987) "Formulation Design and Development of Parenteral Suspensions", Journal of Parenteral Science and Technology, vol. 41, No. 3, pp. 88-96.

(56) References Cited

OTHER PUBLICATIONS

Altamura, et al. (Mar. 1, 2003) "Intramuscular Preparations of Antipsychotics, Uses and Relevance in Clinical Practice", Drugs, vol. 63, No. 5, pp. 493-512.
Alvarez, et al. (Jul. 1989) "Pancreatic Lipase-Catalyzed Hydrolysis of Esters of Hydroxymethyl Phenytoin Dissolved in 1 Various Metabolizable Vehicles, Dispersed in Micellar Systems, and in Aqueous Suspensions", Pharmaceutical Research, vol. 6, Issue 7, pp. 555-563.
Aristada "Prescribing Information Leaflet".
Aulton (1988), Pharmaceutics: The Science of Dosage Form Design, Drug Delivery Systems, pp. 272-274 and 278.
Aulton (1988) "Pharmaceutics: The Science of Dosage Form Design, Drug Delivery Systems.", Chapter 23: Suspensions and Emulsions, pp. 334-359.
Aulton's Pharmaceutics "The Design and Manufacture of Medicines", Third edition. Course Disperse Systems, pp. 90-91 & 386-388.
Barnes, et al. (Jun. 1, 1994) "Long Term Depot Antipsychotics a Risk-Benefit Assessment", Drug Safety, vol. 10, No. 6, pp. 464-479.
Belikov, et al. (1993) "General Chemistry: Pharmaceutical Chemistry", Second Edition, Part 1, pp. 43-45.
Bender, et al. (Feb. 7, 2008) "Cyclopropanecarboxylic Acid Esters as Potential Prodrugs with Enhanced Hydrolytic Stability", Organic letters, vol. 10, No. 3, pp. 509-511.
Berman, et al. (Jun. 2007) "The Efficacy and Safety of Aripiprazole as Adjunctive Therapy in Major Depressive Disorder: A Multicenter, Randomized, Double-Blind, Placebo-Controlled Study", The Journal of clinical psychiatry, vol. 68, No. 6, pp. 843-853.
Blakenship, et al. (Sep. 29, 2010) "Aripiprazole for Irritability Associated with Autistic Disorder in Children and Adolescents Aged 6-17 Years", Pediatric Health, vol. 4, No. 4, pp. 375-381.
Boehme, et al. (Jul. 1966) "Zur Kenntnis der N-[-Alkoxy-alkyl]-carbonsaureamide and der durch ihre thermische Spaltung entstehenden Enamide", Chemische Berichte, vol. 99, No. 7, pp. 2127-2135.
Borthwick, et al. (Jan. 3, 2002) "Design and Synthesis of Pyrrolidine-5,5-trans-lactams (5-Oxohexahydropyrrolo [3,2-b]pyrroles) as Novel Mechanism-Based Inhibitors of Human Cytomegalovirus Protease. 2. Potency and Chirality", Journal of Medicinal Chemistry, vol. 45, No. 1, pp. 1-18.
Bristol Myers Squibb (2005) "Abilify Patient information leaflet FDA".
British National Formulary (2008), "RPS Publishing & BMJ Group", London, vol. 56, pp. 192-197 & 200-201.
Bundgaard, Hans (1985) "Design of Prodrugs: Bioreversible Derivatives for various functional groups and chemical Entities", Chapter 1, Design of Prodrugs. Elsevier Science Ltd, pp. 2-92.
Chang, et al. (Feb. 1996) "Development of a Stable Freeze-Dried Formulation of Recombinant Human Interleukin-1 Receptor Antagonist", Pharmaceutical Research, vol. 13, No. 2, pp. 243-249.
Chueshov, et al. (2002) "Industrial Technology of Medicaments", vol. 1, p. 24.
Cocoman, et al. (Jun. 2008) "Intramuscular Injections: A Review of Best Practice for Mental Health Nurses", Journal of Psychiatric and Mental Health Nursing, vol. 15, No. 5, pp. 424-434.
Collins, et al. (Jan. 1, 2006) "Design and Development of Signal Transduction Inhibitors for Cancer Treatment: Experience and Challenges with Kinase Targets", Current Signal Transduction Therapy, vol. 1, No. 1, pp. 13-23.
Collins, et al. (May 2004) "Novel Pyrrole-Containing Progesterone Receptor Modulators", Bioorganic & Medicinal Chemistry Letters, vol. 14, Issue 9, pp. 2185-2189.
Dai, et al. (May 4, 2007) "Parallel Screening Approach to Identify Solubility-Enhancing Formulations for Improved Bioavailability of a Poorly Water-Soluble Compound Using Milligram Quantities of Material", International Journal of Pharmaceutics, vol. 336, Issue 1, pp. 1-11.

Dezi, Cristina (2007) "Modeling of 5-HT2A and 5-HT2C Receptors and of Their Complexes with Actual and Potential Antipsychotic Drugs", PhD Thesis, Pompeu Fabra University, Barcelona, pp. 1-239.
Doshi, et al. (Nov.-Dec. 2007) In Vivo Pharmacokinetic Studies of Prodrugs of Ibuprofen, Indian Journal of Pharmaceutical, vol. 69, No. 6, pp. 824-827.
Fensome, et al. (Mar. 5, 2008) "Design, Synthesis, and SAR of New Pyrrole-Oxindole Progesterone Receptor Modulators Leading to 5-(7-Fluoro-3,3-Dimethyl-2-Oxo-2,3-Dihydro-1H-Indol-5-yl)-1-Methyl-1H-Pyrrole-2-Carbonitrile (WAY-255348)", Journal of Medicinal Chemistry, vol. 51, No. 6, pp. 1861-1873.
Girouard, et al. (Jan. 1, 2006) "Neurovascular Coupling in the Normal Brain and in Hypertension, Stroke, and Alzheimer Disease", Journal of Applied Physiology, vol. 100, No. 1, pp. 328-335.
Glick, et al. (May-Jun. 2001) "Treatment with Atypical Antipsychotics: New Indications and New Populations", Journal of Psychiatric Research, vol. 35, No. 3, pp. 187-191.
Gowda, et al. (2013) "Development and Characterization of Ground Mixtures of Aripiprazole with Hydrophilic Carriers", International Journal of Pharmaceutical Research and Bio-Science, vol. 2, No. 6, pp. 537-556.
Hartung, et al. (Jan. 2009) "A Simple and Efficient Preparation of Novel Formaldehyde Derivatives", Synthesis, No. 3, pp. 495-501.
Harvey, et al. (Feb. 1, 2005) "Ziprasidone: Efficacy, Tolerability, and Emerging Data on Wide-Ranging Effectiveness", Expert Opinion on Pharmacotherapy, vol. 6, No. 2, pp. 337-346.
Hutchings, et al. (Feb. 1996) "An Oxazoline-Mediated Synthesis of the Pyrrolophenanthridine Alkaloids and Some Novel Derivatives,", The Journal of Organic Chemistry, vol. 61, No. 3, pp. 1004-1013.
Iley, et al. (Nov. 1, 1997) "Acyloxymethyl as a Drug Protecting Group: Part 4. The Hydrolysis of Tertiary Amidomethyl Ester Prodrugs of Carboxylic Acid Agents,", Pharmaceutical Research, vol. 14, No. 11, pp. 1634-1639.
Kearney, Albert S. (May 22, 1996) "Prodrugs and Targeted Drug Delivery", Advanced Drug Delivery Reviews, vol. 19, No. 2, pp. 225-239.
Keck, et al. (Jan. 2009) "Aripiprazole Monotherapy in the Treatment of Acute Bipolar I Mania: A Randomized, Double-Blind, Placebo- and Lithium-Controlled Study", Journal of Affective Disorders, vol. 112, Issues 1-3, pp. 36-49.
Kesisoglou, et al. (Jul. 30, 2007) "Nanosizing: Oral Formulation Development and Biopharmaceutical Evaluation", Advanced Drug Delivery Reviews, vol. 59, No. 7, pp. 631-633.
Kim, et al. (Jul. 1991) "A New Class of Acyclic Phosphonate Nucleotide Analogs: Phosphonate Isosteres of Acyclovir and Ganciclovir Monophosphates as Antiviral Agents", Journal of Medicinal Chemistry, vol. 34, No. 7, pp. 2286-2294.
Kong, et al. (Oct. 5, 2003) "Simultaneous determination of 3'-azido-2',3'-dideoxyuridine and novel prodrugs in rat plasma by liquid chromatography", Journal of Chromatography B, vol. 795, Issue 2, pp. 371-376.
Krise, et al. (Aug. 12, 1999) "Novel Pro Drug Approach for Tertiary Amines Synthesis and Preliminary Evaluation of N-Phosphonooxymethyl Prodrugs,", Journal of Medicinal Chemistry, vol. 42, No. 16, pp. 3094-3100.
Leonard, et al. (1995) "Advanced Practical Organic Chemistry", 2nd Edition, Chapter 9, pp. 128-226.
Lieberman, et al. (1997) "Pharmaceutical Dosage Forms: Disperse Systems", vol. 2, pp. 18-22, 285-301.
Lin, et al. (Aug. 15, 2008) "Diazonamide Support Studies: Stereoselective Formation of the C10 Chiral Center in both the CDEFG and AEFG Fragments", Organic Letters, vol. 10, No. 18, pp. 3969-3972.
Link et al., (Dec. 5, 1994) "Regioselective Imide Reduction: An Issue in the Total Synthesis of Staurosporine", Tetrahedron Letters, vol. 35, No. 49, pp. 9135-9138.
Link, et al. (Jan. 1995) "First Total Synthesis of Staurosporine and ent-Staurosporine", Journal of the American Chemical Society, vol. 117, No. 1, pp. 552-553.
Link, et al. (Mar. 27, 1996) "Staurosporine and ent-Staurosporine: The First Total Syntheses, Prospects for a Regioselective Approach, and Activity Profiles", Journal of the American Chemical Society, vol. 118, No. 12, pp. 2825-2842.

(56) References Cited

OTHER PUBLICATIONS

Lopes, et al. (Jan. 1, 1999) "Acyloxymethyl as a Drug Protecting Group. Part 5.1 Kinetics and Mechanism of the Hydrolysis of Tertiary N-Acyloxymethylsulfonamides", Perkin Transactions 2: Physical Organic Chemistry, vol. 2, No. 3, pp. 431-439.
Lozhkin, et al. (Mar.-Apr. 2007) "The First Conglomerate in the series of 2,4,6,8, 10-Pentaazatricyclo[5.3.1.03.11] undecane-1,5-Diones", Mendeleev Communications, vol. 17, Issue 2, pp. 85-87.
Lund, W (Jan. 30, 2009) "The Pharmaceutical Codex", Twelth Edition, Suspensions, pp. 72-87.
MacKenzie, et al. (Mar. 29, 1977) "Non-Equilibrium Freezing Behaviour of Aqueous Systems [and Discussion]", Philosophical Transactions of the Royal Society of London. Series B, Biological Sciences, vol. 278, No. 959, pp. 167-189.
Marszall, et al. (Feb. 1982) "The Effect of Glycols on the Hydrophile-Lipophile Balance and the Micelle Formation of Nonionic Surfactants", Journal of the American Oil Chemists' Society, vol. 59, No. 2, pp. 84-87.
McCaron, et al. (Feb. 4, 2008) "Incorporation of Novel 1-Alkylcarbonyloxymethyl Prodrugs of 5-Fluorouracil into Poly(Lactide-Co-Glycolide) Nanoparticles", International Journal of Pharmaceutics, vol. 348, Issues 1-2, pp. 115-124.
Miao, et al. (Jul. 2005) "Characterization of a Novel Metabolite Intermediate of Ziprasidone in Hepatic Cylosolic Fractions of Rat, Dog, and Human by ESI-MS/MS, Hydrogen/Deuterium Exchange, and Chemical Derivatization", Drug Metabolism and Disposition, vol. 33, No. 7, pp. 879-883.
Mizutani, et al. (Nov. 2009) "Discovery of Novel Benzoxazinones as Potent and Orally Active Long Chain Fatty Acid elongase 6 Inhibitors", Journal of medicinal chemistry, vol. 52, No. 22, pp. 7289-7300.
Morales, et al. (2012) "Mechanical Particle-Size Reduction Techniques", AAPS Advances in Pharmaceutical Sciences Series: Formulating Poorly Water Soluble Drugs, pp. 133-170.
Naber, et al. (Dec. 2004) "Aripiprazole: A New Atypical Antipsychotic with a Different Pharmacological Mechanism", Progress in Neuro-Psychopharmacology and Biological Psychiatry, vol. 28, Issue 8, pp. 1213-1219.
Niele, et al. (Jan. 1988) "Palladium(II) cage compounds based on diphenylglycoluril", Journal of the American Chemical Society, vol. 110, No. 1, pp. 172-177.
Niele, et al. (Mar. 1989) "Rhodium (III) cage compounds based on diphenylglycoluril", Journal of the American Chemical Society, vol. 111, No. 6, pp. 2078-2085.
Nielsen, et al. (Apr. 2005) "Bioreversible Quaternary N-Acyloxymethyl Derivatives of the Tertiary Amines Bupivacaine and 2 Lidocaine-Synthesis, Aqueous Solubility and Stability in Buffer, Human Plasma and Simulated Intestinal Fluid", European Journal of Pharmaceutical Sciences, vol. 24, Issue 5, pp. 433-440.
Nomura, et al. (Feb. 22, 1999) "(3-Substituted Benzyl) Thiazolidine-2,4-Diones as Structurally New Antihyperglycemic Agents", Bioorganic & Medicinal Chemistry Letters, vol. 9, Issue 4, pp. 533-538.
O'Brien, et al. (Feb. 1, 2003) "Vascular Cognitive Impairment", The Lancet Neurology vol. 2, No. 2, pp. 89-98.
Palin, et al. (Mar. 15, 2008) "Structure-Activity Relationships and CoMFA of N-3 Substituted Phenoxypropyl Piperidine Benzimidazol-2-One Analogues as NOP Receptor Agonists with Analgesic Properties", Bioorganic & Medicinal Chemistry, vol. 16, Issue 6, pp. 2829-2851.
Park, et al. (Apr. 30, 1999) "Preparation and Evaluation of Flurbiprofen-Loaded Microemulsion for Parenteral Delivery", International Journal of Pharmaceutics, vol. 181, No. 2, pp. 173-179.
Pass, et al. (Jun. 21, 1999) "Thrombin Inhibitors Based on [5,5] Trans-Fused Indane Lactams", Bioorganic & Medicinal Chemistry Letters, vol. 9, Issue 12, pp. 1657-1662.
Pitman, Ian H. (Jun. 1981) "Pro-Drugs of Amides, Imides, and Amines", Medicinal Research Reviews, vol. 1, No. 2, pp. 189-214.
Porras, et al. (Nov. 30, 2004) "Studies of Formation of W/O Nano-Emulsions", Colloids and Surfaces A: Physicochemical and Engineering Aspects, vol. 249, Issues 1-3, pp. 115-118.
Rautio, et al. (Mar. 2008) "Prodrugs: Design and Clinical Applications", Nature Reviews, vol. 7, No. 3, pp. 255-270.
Redden, et al. (Apr. 15, 1999) "Acyloxymethyl Acidic Drug Derivatives: In Vitro Hydrolytic Reactivity", International Journal of Pharmaceutics, vol. 180, No. 2, pp. 151-160.
Robinson, et al. (Jan. 5, 1996) "Discovery of the Hemifumarate and (alpha-L-Alanyloxy)methyl Ether as Prodrugs of Antirheumatic Oxindole: Prod rugs for the Enolic OH Group", Journal of Medicinal Chemistry, vol. 39, No. 1, pp. 10-18.
Rowe, et al. "Extract for Sorbitan Esters", Handbook of Pharmaceutical Excipients, Sixth Edition, pp. 675-678.
Rowe, et al. "Extract for Sorbitan Esters", Handbook of Pharmaceutical Excipients, Fifth edition, pp. 473-476.
Rowley, et al. (Feb. 15, 2001) "Current and Novel Approaches to the Drug Treatment of Schizophrenia", Journal of medicinal chemistry, vol. 44, No. 4, pp. 477-501.
Sajatovic, Martha (Jul. 1, 2003) "Treatment for Mood and Anxiety Disorders: Quetiapine and Aripiprazole", Current Psychiatry Reports, vol. 5, No. 4, pp. 320-326.
Schmidt, et al. (Aug. 17, 2001) "Ziprasidone: a Novel Antipsychotic Agent with a Unique Human Receptor Binding Profile", European Journal of Pharmacology, vol. 425, No. 3, pp. 197-201.
Shah, et al. (Apr.-May 2008) "Current Approaches in the Treatment of Alzheimer's Disease", Biomedicine & Pharmacotherapy, vol. 62, Issue 4, pp. 199-207.
Shinde, et al. (Feb. 2011) "Microemulsions and Nanoemulsions for Targeted Drug Delivery to the Brain", Current Nanoscience, vol. 7, No. 1, pp. 119-133.
Shintani, et al. (Sep. 1967) "A New Method to Determine the Irritation of Drugs After Intramuscular Injection in Rabbits", Toxicology and Applied Pharmacology, vol. 11, Issue 2 IN1, 296-301, pp. 293-295.
Siegel, (Jun. 2005) "Extended Release Drug Delivery Strategies in Psychiatry—Theory to Practice", Psychiatry, Edgmont, vol. 2, No. 6, pp. 22-31.
Simplicio, Ana Luisa. (May 24, 20047) "Beta-Aminoketones as Prodrugs with pH-Controlled Activation", International Journal of D Pharmaceutics, vol. 336, No. 2, pp. 208-214.
Simplicio, et al. (Mar. 3, 2008) "Prodrugs for Amines", Molecules, vol. 13, No. 3, pp. 519-547.
Skinner, et al. (Apr. 1977) "Topical Mosquito Repellents X: 2-Oxazolidones", Journal of Pharmaceutical Sciences, vol. 66, Issue 4, pp. 587-589.
Stella, et al. (Jun. 12, 2000) "Aqueous Solubility and Dissolution Rate Does Not Adequately Predict in Vivo Performance: A probe Utilizing Some N-AcylOxymethyl Phenyloin Prodrugs", Journal of Pharmaceutical Sciences, vol. 88, No. 8, pp. 775-779.
Stella, et al. (2007) "Pro Drugs: Challenges and Rewards", Part 1, Springer, New York, Chapter 2.4.1.
Strickley, Robert G. (2004) "Solubilizing Excipients in Oral and Injectable Formulations", Pharmaceutical Research, vol. 21, No. 2, pp. 201-230.
Tang, et al. (Feb. 2004) "Design of Freeze-Drying Processes for Pharmaceuticals: Practical Advice", Pharmaceutical Research, vol. 21, Issue 2, pp. 191-200.
Varma, et al. (Jan. 1968) "Synthesis and Antibacterial Activity of Certain 3-Substituted Benzoxazolines", Journal of Pharmaceutical Sciences, vol. 57, Issue 1, pp. 39-44.
Weiler, et al. (1976) "Isothiazoles VII: N-Hydroxyalkylation and Mannich Reaction of 4-Isothiazolin-3-one", Journal of chemistry, vol. 13, No. 5, pp. 1097-1098.
Weitzel, et al. (1963) "Weitere Tumorhemmende Verbindungsklassen, I Cytostatische Effekte von N-and SHydroxymethyl-Verbindungen", Hoppe-Seyler's Zeitschrift Fur Physiologische Chemie, vol. 334, No. 1, pp. 1-25.
Wermuth, Camille G. (1996) "Designing Prodrugs and Bioprecursors: Carrier Prodrugs", The Practice of Medicinal Chemistry, pp. 680-681.
White, et al. (2002) "Correlation between Anticonvulsant Activity and Inhibitory Action of Glial gamma-Aminobutyric Acid Uptake of the Highly Selective Mouse gamma-Aminobutyric Acid Transporter 1 Inhibitor 3-Hydroxy-4-amino-4, 5, 6, 7- and its N-alkylated

(56) References Cited

OTHER PUBLICATIONS

Analogs", The Journal of Pharmacology and Experimental Therapeutics, vol. 302, No. 2, pp. 636-644.
Wong, et al. (Jun. 15, 1989) "Unsaturated cyclic ureas as new non-toxic biodegradable transdermal penetration enhancers. I Evaluation study", International Journal of Pharmaceutics, vol. 52, No. 3, pp. 191-202.
Workman (1999) "Safe Injection Techniques", Nursing Standard, vol. 13, No. 39, pp. 47-53.
World Health Organization (2003) "Annex 9 Guide to Good Storage Practices for Pharmaceuticals", WHO Technical Report Series, No. 908, 12 Pages.
Yamada, Shozo (1962) "Oxidation Products of Hydroxylycoctonam", Bulletin of the Chemical Society of Japan, vol. 35, Issue 4, pp. 670-672.
Yates, et al. (1995) "1,3-Dipolar Cycloadditions to Oxidopyraziniums", Heterocycles, vol. 40, No. 1, pp. 831-347.
Yoda, et al. (2001) "Sml2-Mediated Hetero-Coupling Reaction of Lactams with Aldehydes; Synthesis of Indolizidine Alkaloids, (-)-δ-Coniceine, (+)-5-Epiindolizidine 167B and (+)-Lentiginosine", Tetrahedron Letters, vol. 42, No. 13, Abstract only, pp. 2509-2512.
Young, et al. (1996) "The Neuroleplic Treatment of Schizophrenia: Dosing Strategies, Depot Preparations and Novel Medications", Jefferson Journal of Psychiatry, vol. 13, No. 1, pp. 18-26.
Zinner, et al. (1975) "Benzazole, XXIX. [2-Oxo-benzoxazolyl-(3)-methyl]-ester von Carbonsäuren und Thiocarbonsäuren", Journal fur Praktische Chemie, vol. 317, No. 3, pp. 379-386.
U.S. Appl. No. 16/248,259, filed Jan. 15, 2019, Janson M. Perry.
U.S. Appl. No. 14/714,621, 2015/0258115, U.S. Pat. No. 9,351,976, filed May 18, 2015, Sep. 17, 2015, May 31, 2016, Janson M. Perry.
U.S. Appl. No. 13/801,025, 2015/0267503, U.S. Pat. No. 10,004,807, filed Mar. 13, 2013, Oct. 10, 2013, Jun. 26, 2018, Janson M. Perry.
U.S. Appl. No. 13/801,167, 2013/0267504, U.S. Pat. No. 9,993,556, filed Mar. 13, 2013, Oct. 10, 2013, Jun. 12, 2018, Janson M. Perry.
U.S. Appl. No. 13/801,344, 2013/0267505, U.S. Pat. No. 9,999,670, filed Mar. 13, 2013, Oct. 10, 2013, Jun. 19, 2018, Janson M. Perry.
U.S. Appl. No. 16/425,150, 2019-0275155, U.S. Pat. No. 10,639,376, filed May 29, 2019, Sep. 12, 2019, May 5, 2020, Janson M. Perry.
U.S. Appl. No. 16/834,565, 2020/0268891, U.S. Pat. No. 11,097,006, filed Mar. 30, 2020, Aug. 27, 2020, Aug. 24, 2021, Janson M. Perry.
U.S. Appl. No. 17/398,801, filed Aug. 10, 2021, Jason M. Perry.
U.S. Appl. No. 16/271,248, 2019-0167673, U.S. Pat. No. 10,478,434, filed Feb. 8, 2019, Jun. 6, 2019, Nov. 19, 2019, Magali B. Hickey.
U.S. Appl. No. 16/889,528, 2020-0289504, filed Jun. 1, 2020, Jul. 17, 2020, Magali B. Hickey.
U.S. Appl. No. 16/043,721, 2019/0015408, filed Jul. 24, 2018, Jan. 17, 2019, Wilfredo Morales.
U.S. Appl. No. 16/425,119, 2019-0276406, U.S. Pat. No. 10,822,306, filed May 29, 2019, Sep. 12, 2019, Nov. 3, 2020, Julius F. Remenar.
U.S. Appl. No. 17/020,499, 2020-0407320, filed 09-14-020 Dec. 31, 2020, Julius F. Remenar.
U.S. Appl. No. 16/023,887, 2019/0031648, U.S. Pat. No. 10,428,058, filed Jun. 29, 2018, Jan. 31, 2019, Oct. 1, 2019, Laura Cook Blumberg.
U.S. Appl. No. 16/540,802, 2019-0367501, U.S. Pat. No. 10,723,728, filed Aug. 14, 2019, 12/I05/2019, Jul. 28, 2020, Laura Cook Blumberg.
U.S. Appl. No. 16/291,768, 2019-0298716, filed Mar. 4, 2019, Oct. 3, 2019, Lisa L. von Moltke.
Alkermes: "Aristada—Highlights of Prescribing Information", pp. 1-35 (2015).
Cruz et al., "Aripiprazole Lauroxil (Aristada), An Extended-Release, Long-Acting Injection for the Treatment of Schizophrenia", *Pharmacy & Therapeutics* 41(9):556-559 (2016).
Jain et al., "Size matters: the importance of particle size in a newly developed injectable formulation for the treatment of schizophrenia", *CNS Spectrums* 25(3):323-330 (2019).

\* cited by examiner

ARIPIPRAZOLE DOSING STRATEGY

CROSS-REFERENCE TO RELATED APPLICATIONS

This application is a continuation of U.S. patent application Ser. No. 16/291,768, filed Mar. 4, 2019, which claims priority to U.S. Provisional Patent Application No. 62/638,587, filed Mar. 5, 2018. The entire content of this application is incorporated herein by reference in its entirety.

BACKGROUND

Schizophrenia is a severe neuropsychiatric illness with onset in late adolescence or early adulthood. Typified by distorted perceptions of reality (hallucinations and delusions), social deficits, disorganized language and behavior, and mild cognitive dysfunction, it is a devastating and relatively common disorder, affecting about 1% of worldwide populations.

Patients with schizophrenia require long-term antipsychotic therapy, and one limitation of long-acting injectable (LAI) antipsychotic therapy is that some LAI regimens require oral lead-in (initiation) regimens lasting 2-3 weeks to achieve initial therapeutic concentrations. See, e.g., Brissos, S., et al. *Therapeutic Advances in Psychopharmacology*, 2014, 4(5), 198-219; Citrome, L. Expert Review of Neurotherapeutics, 2017, 17(10), 1029-1043. These oral lead-in regimens can be challenging for patients who do not want to take pills, or when a patient initiates LAI therapy in a hospital but is required to continue the oral lead-in for some time after hospital discharge.

Accordingly, there exists a need for improved methods of delivering antipsychotics, thereby improving patient compliance and maximizing the pharmacological profile of the active agent.

SUMMARY

Provided herein are methods for treating schizophrenia in a subject in need thereof, comprising administering to the subject a combination of aripiprazole, a nanoparticle dispersion of aripiprazole lauroxil ($AL_{NCD}$), and an LAI of aripiprazole lauroxil. Conventional administration of an LAI of aripiprazole lauroxil requires a 21-day oral lead-in of aripiprazole (initiation). In contrast, the combination described herein requires only a 1-3 day oral aripiprazole lead-in time. This minimized lead-in time has a number of advantages, including increased patient compliance.

Accordingly, in one aspect, provided herein is a method of treating schizophrenia in a subject in need thereof, the method comprising administering to the subject, in any order:

a first component comprising about 5-50 mg of aripiprazole;

a second component comprising about 629-695 mg of $AL_{NCD}$; and a third component comprising a therapeutically effective amount of aripiprazole lauroxil.

In an embodiment, the components of the invention can be administered in any order.

In an embodiment, all components are pharmaceutical compositions comprising the active ingredients listed above and pharmaceutically acceptable carriers.

In an embodiment, the $AL_{NCD}$ comprises polysorbate 20, sodium citrate, sodium chloride, an aqueous buffer, and a population of particles of aripiprazole lauroxil. In another embodiment, the population of particles of aripiprazole lauroxil has a volume-based particle distribution size (Dv50) of less than about 1000 nm. In an embodiment, the population of particles of aripiprazole lauroxil has a volume-based particle distribution size (Dv50) between about 175 nm and about 350 nm. In an embodiment, the $AL_{NCD}$ has a ratio of particles to polysorbate 20 between about 0.1:1 and about 40:1. In an embodiment, the $AL_{NCD}$ has a ratio of particles to polysorbate 20 of 17:1. In an embodiment, the $AL_{NCD}$ comprises about 26 weight percent aripiprazole lauroxil particles, about 1.53 weight percent polysorbate 20, about 0.76 weight percent sodium citrate, 0.31 weight percent sodium chloride, and an aqueous buffer; wherein the particles of aripiprazole lauroxil have a volume-based particle distribution size (Dv50) between about 175 nm and about 350 nm.

In one embodiment, the first component is administered at a dosage of about 30 mg of aripiprazole. In another embodiment, the first component is administered at a dosage of about 15 mg of aripiprazole. In yet another embodiment, the second component is administered at a dosage of about 675 mg of aripiprazole lauroxil. In another embodiment, the second component is administered at a dosage of about 677 mg of aripiprazole lauroxil. In still another embodiment, the third component is administered at a dosage of about 300-1500 mg aripiprazole lauroxil. In an embodiment, the third component is administered at a dosage of 441, 662, 882, or 1064 mg.

The components can be administered at substantially the same time (i.e., generally within minutes of each other, or within the time it takes a person of ordinary skill in the medical or pharmaceutical arts to administer the components). In one embodiment, all components of the method are administered at substantially the same time. In another embodiment, the method comprises a regimen wherein the first, second, and third components are administered at substantially the same time, and wherein the first component is not administered again within 21 days of the initial administration. In yet another embodiment, the method comprises a regimen wherein the first, second, and third components are administered at substantially the same time, and wherein the second administration of the components occurs no earlier than 21 days after the initial treatment. In still another embodiment, the method comprises a regimen wherein the first, second, and third components are administered at substantially the same time, followed by a second treatment comprising administering the third component alone. In an embodiment, the second treatment of any or all of the components occurs no earlier than 21 days after the initial treatment. In an embodiment, the first component is only administered once during the treatment duration. In an embodiment, the first component is not administered again within 21 days following the initial treatment.

In an embodiment, the method comprises a regimen wherein the first component is only administered on the first and/or second days of treatment, the second component is only administered on the first day of treatment, and the third component is only administered once within the first 10 days of treatment. In another embodiment, the regimen further comprises a second administration of the third component alone. In yet another embodiment, the third component is administered on the first day of treatment. In still another embodiment, the third component is administered on the second day of treatment. In an embodiment, the third component is administered 7-10 days after the start of the treatment regimen. In another embodiment, the third component is administered 3-6 days after the start of the treatment regimen. In yet another embodiment, the first component is only administered on the first and second day of treatment. In still another embodiment, the first component is only administered on the first day of treatment.

In one embodiment, the first component is administered orally. In an embodiment, the second component is administered intra-muscularly. In an embodiment, the second component is administered intra-muscularly to the deltoid or gluteus. In an embodiment, the second component is administered intra-muscularly to the deltoid. In an embodiment, the third component is administered intra-muscularly. In an embodiment, the third component is administered intra-muscularly to the deltoid or gluteus.

In another aspect, provided herein is a method of treating schizophrenia in a subject in need thereof, the method comprising administering to the subject:
a first component comprising aripiprazole;
a second component comprising $AL_{NCD}$; and
a third component comprising aripiprazole lauroxil;
wherein the dosages of the first, second, and third components combined are sufficient to maintain a therapeutically effective mean blood plasma level of aripiprazole in the subject. FIG. 8 shows mean blood plasma levels obtained using the instant methods.

In an embodiment, the therapeutically effective mean blood plasma level of aripiprazole is about 102-435 ng/mL at steady-state plasma level. In an embodiment, the therapeutically effective mean blood plasma level of aripiprazole is greater than about 102 ng/mL at steady-state plasma level. In an embodiment, the therapeutically effective mean blood plasma level of aripiprazole is less than about 435 ng/mL at steady-state plasma level. In an embodiment, the therapeutically effective mean blood plasma level of aripiprazole is between about 102 ng/mL and about 435 ng/mL at steady-state plasma level. In an embodiment, the therapeutically effective mean blood plasma level of aripiprazole is reached within 24 hours of the initial treatment. In an embodiment, the therapeutically effective mean blood plasma level of aripiprazole is maintained for no less than 21 days.

In another aspect, provided herein is a kit for the treatment of schizophrenia, wherein the kit comprises therapeutically effective amounts of:
a first component comprising aripiprazole;
a second component comprising $AL_{NCD}$; and
a third component comprising aripiprazole lauroxil;
and further comprises instructions for administration, wherein the instructions specify oral administration of the first component, intra-muscular administration of the second component, and intra-muscular administration of the third component.

DETAILED DESCRIPTION

Aripiprazole lauroxil (AL), a prodrug of the atypical antipsychotic aripiprazole, is available as a long-acting intramuscular (IM) injection indicated for the treatment of schizophrenia. See, e.g., Meltzer, H. Y., et al., *J. Clin. Psychiatry*, 2015, 76(8), 1085-1090. Treatment with AL can be initiated in a patient at any of the four available doses: 441 mg, 662 mg, 882 mg, or 1064 mg. The dissolution properties of AL allow for long dose intervals. For example, there exists a 1064 mg AL dose that is specifically indicated as a 2-month dose interval option. The slow dissolution of AL results in an initial delay between the first AL injection and the attainment of effective concentrations of aripiprazole. Currently, 21 days of oral aripiprazole supplementation are required with the first AL dose to provide adequate antipsychotic coverage during treatment initiation.

The 21-day oral requirement poses challenges in that, as an oral medication, it can be stopped prematurely. In the context of starting AL, premature discontinuation of the oral aripiprazole supplementation at initiation can lead to a drop in aripiprazole levels below therapeutic plasma concentrations. Therefore, there remains a need to provide an alternative initiation regimen for AL without the need for continued oral supplementation.

Figure 8:
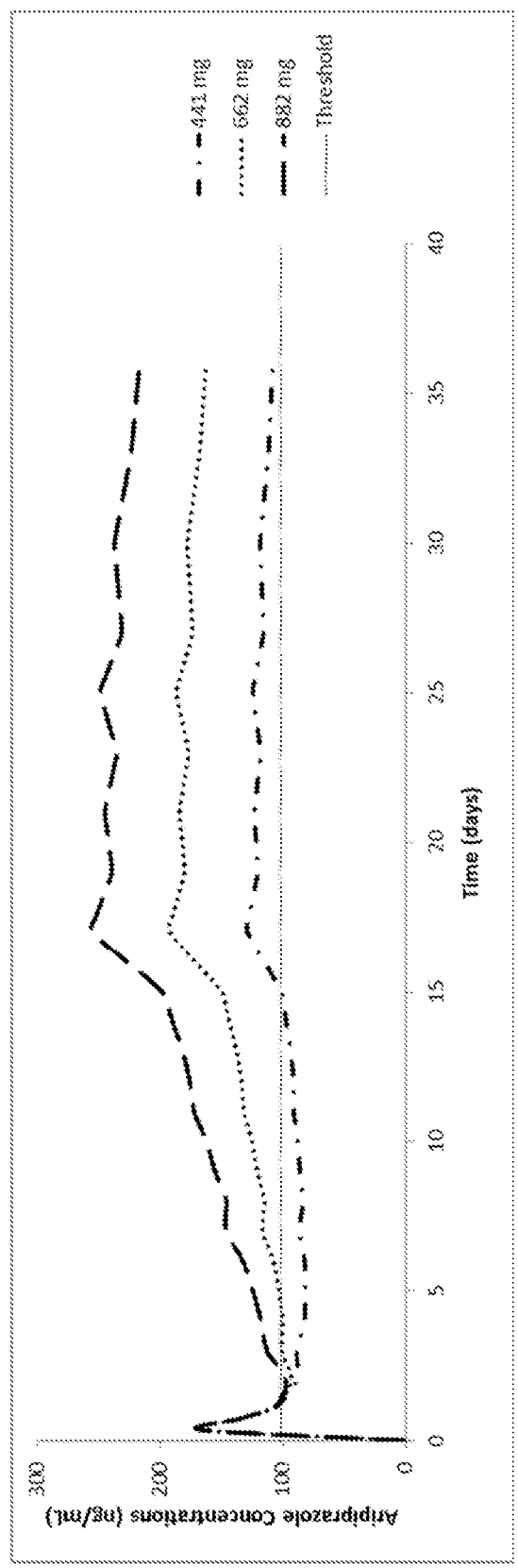
FIG. 8: Simulated Aripiprazole concentrations following a single injection of $AL_{NCD}$ at the dose provided in the legend along with a 50 mg IM administration of aripiprazole. The 662 mg dose provides enough coverage to keep concentrations above the minimum threshold.

The instantly described combination and dosing strategies address this need. Phase 1 pharmacokinetic (PK) studies show that $AL_{NCD}$ with a single 30 mg oral aripiprazole tablet on one day (1-day initiation regimen) provides aripiprazole plasma concentrations similar to the 21-day initiation regimen when starting AL 441 or 882 mg. Thus, provided herein is a method of treating schizophrenia in a subject in need thereof, the method comprising administering to the subject: a first component comprising aripiprazole; a second component comprising $AL_{NCD}$; and a third component comprising a therapeutically effective amount of aripiprazole lauroxil. In an embodiment, the first component is administered at a dosage of about 30 mg, the second component is administered at a dosage of about 675 mg, and the third component is administered at a dosage of 441, 662, 882, or 1064 mg. In yet another an embodiment, the first component is administered at a dosage of about 30 mg, the second component is administered at a dosage of about 677 mg, and the third component is administered at a dosage of 441, 662, 882, or 1064 mg. In another embodiment, the dosages of the first, second, and third components combined are sufficient to maintain a therapeutically effective mean blood plasma level of aripiprazole in the subject. The threshold for a therapeutically effective mean blood plasma level of aripiprazole is about 102 ng/mL. FIG. 8 shows that the 662 and 882 mg dosages of $AL_{NCD}$, in combination with aripiprazole and aripiprazole lauroxil, afford mean blood plasma levels above the threshold.

Figure 7A:
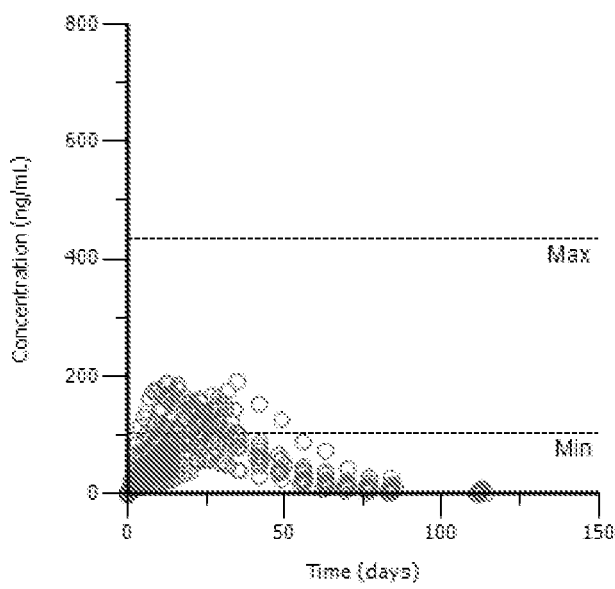
FIG. 7A: Scatterplot of aripiprazole concentrations following a single injection of $AL_{NCD}$ at the 441 mg dose relative to minimum and maximum thresholds established by the FDA.
Figure 7B:
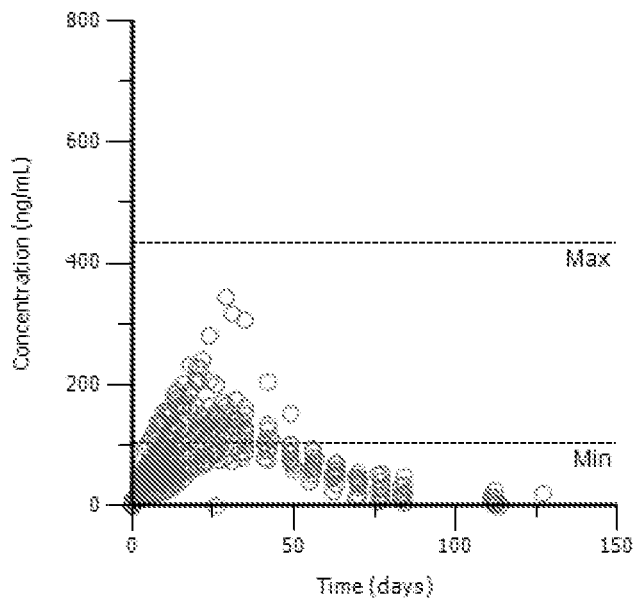
FIG. 7B: Scatterplot of aripiprazole concentrations following a single injection of $AL_{NCD}$ at the 662 mg dose relative to minimum and maximum thresholds established by the FDA.
Figure 7C:
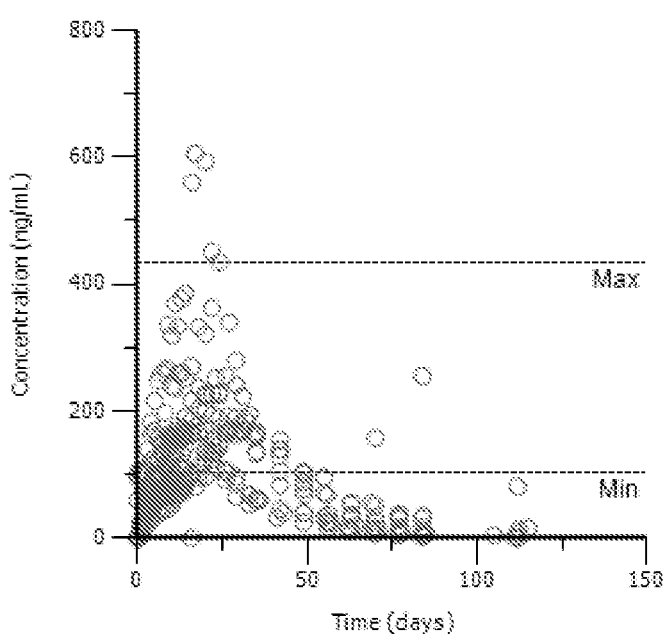
FIG. 7C: Scatterplot of aripiprazole concentrations following a single injection of $AL_{NCD}$ at the 882 mg dose relative to minimum and maximum thresholds established by the FDA.

The FDA has also established a maximum threshold for an acceptable mean blood plasma level of 435 ng/mL. FIGS. 7A, 7B, and 7C show scatterplots of mean blood plasma levels of aripiprazole after injections of $AL_{NCD}$ alone at dosages of 441 mg (FIG. 7A), 662 mg (FIG. 7B), and 882 mg (FIG. 7C). As evidenced by these figures, the 882 mg dose of $AL_{NCD}$ results in mean blood plasma levels above the maximum level recommended by the FDA.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

As used herein, the term "treat," "treated," "treating," or "treatment" includes the diminishment or alleviation of at least one symptom associated with or caused by the state, disorder or disease being treated. For example, treatment can be diminishment of one or several symptoms of a disorder.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "use" includes any one or more of the following embodiments of the invention, respectively: the use in the treatment of schizophrenia, the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise.

As used herein, the term "patient," "individual," or "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from, schizophrenia. In another embodiment, the subject is a cell.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. The term "individual" does not denote a particular age or sex.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The terms "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

As used herein, the term "weight percent" is meant to refer to the quantity by weight of a compound and/or component in a composition as the quantity by weight of a constituent component of the composition as a percentage of the weight of the total composition. The weight percent can also be calculated by multiplying the mass fraction by 100. The "mass fraction" is the ratio of one substance of a mass $m_1$ to the mass of the total composition $m_T$ such that weight percent=$(m_1/m_T)*100$.

"Aqueous buffer" refers to a water solution which resists change in hydronium ion and the hydroxide ion concentration (and consequent pH) upon addition of small amounts of acid or base, or upon dilution. Buffer solutions consist of a weak acid and its conjugate base (more common) or a weak base and its conjugate acid (less common). The buffer can be prepared by methods well known in the art with the appropriate buffering agents to give the desired pH value. Examples of the suitable buffering agents include hydrochloric acid, lactic acid, acetic acid, citric acid, malic acid, maleic acid, pyruvic acid, succinic acid, tris-hydroxymethylaminomethane, sodium hydroxide, sodium bicarbonate, phosphoric acid, sodium phosphate, and other biologically acceptable buffering agents. Aqueous buffers are readily available commercially and they can be used in preparation of the compositions of this invention without further treatment. The "mean blood plasma level" of a substance, as used herein, refers to the mean level of the substance found in multiple plasma samples. The mean blood plasma level is obtained by adding the concentrations of the substance found in the plasma samples then dividing the sum by the number of plasma samples.

As used herein, "steady-state plasma level" is intended to indicate the total exposure (AUC) over 1 dosing interval (at steady-state) divided by the time of the dosing interval. So while concentrations rise and fall during a dosing interval at steady state, the average concentration does not change. Once at steady-state, every dose would give the same maximum serum concentration (Cmax), minimum serum concentration (Cmin), area under the curve (AUC), and steady state concentration (Css), such that Css=AUC/dosing interval.

Pharmaceutical Compositions

Disclosed herein is a method and dosing regimen for treating schizophrenia in a subject in need thereof, the method comprising administering to the subject a first component comprising aripiprazole. U.S. Pat. Nos. 4,734,416 and 5,006,528 disclose aripiprazole, 7-{4-[4-(2,3-dichlorophenyl)-1-piperazinyl]butoxy}-3,4-dihydro-2(1H)-quinolinone or 7-{4-[4-(2,3-dichlorophenyl)-1-piperazinyl]butoxy}-3,4-dihydro carbostyril, as an atypical antipsychotic agent useful in the treatment of schizophrenia, bipolar disease, depression, and other CNS disorders. These documents are incorporated herein by reference in their entireties. Aripiprazole has the following chemical structure:

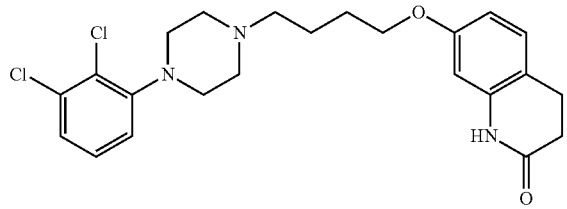

Aripiprazole is sold under the trade name ABILIFY®. It acts as a dopamine D2 partial agonist, serotonin 5-HT1A receptor agonist, and is an antagonist of the serotonin 5-HT2A receptor. ABILIFY® is currently administered orally on a once-a-day dosing schedule as ABILIFY® (aripiprazole) Tablets, ABILIFY DISCMELT® (aripiprazole) Orally Disintegrating Tablets, and ABILIFY® (aripiprazole) Oral Solution. In an embodiment, the aripiprazole component is a pharmaceutical composition comprising aripiprazole and a pharmaceutically acceptable carrier.

The method and dosing regimen also comprises the component aripiprazole lauroxil. U.S. Pat. Nos. 8,431,576, 8,796,276, 9,034,867, 9,193,685, 9,452,131, and 9,526,726 disclose aripiprazole lauroxil, (7-(4-(4-(2,3-dichlorophenyl)piperazin-1-yl)butoxy)-2-oxo-3,4-dihydroquinolin-1(2H)-yl)methyl dodecanoate, as an extended release prodrug of aripiprazole useful in the treatment of schizophrenia, bipolar disease, depression, and other CNS disorders. These documents are incorporated herein by reference in their entireties. Aripiprazole lauroxil has the following chemical structure:

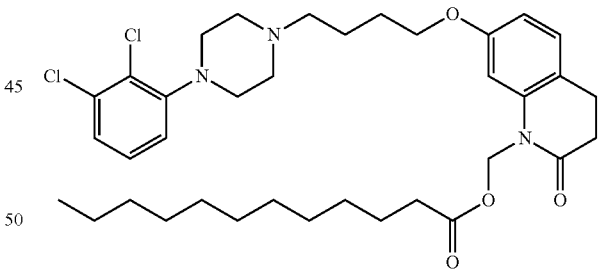

Aripiprazole lauroxil is sold under the trade name ARISTADA®, and is currently administered intra-muscularly.

In an embodiment, the aripiprazole lauroxil component is a pharmaceutical composition comprising aripiprazole lauroxil and a pharmaceutically acceptable carrier. In an embodiment, the aripiprazole lauroxil component is a pharmaceutical composition comprising aripiprazole lauroxil, sorbitan laurate, polysorbate 20, and an aqueous vehicle.

The method and dosing regimen also comprises a component that is a nanoparticle dispersion of aripiprazole lauroxil ($AL_{NCD}$). U.S. Pat. No. 10,016,415 discloses $AL_{NCD}$. $AL_{NCD}$ is a pharmaceutical composition comprising polysorbate 20, sodium citrate, sodium chloride, an aqueous buffer, and a population of particles of aripiprazole lauroxil useful in the treatment of schizophrenia, bipolar disease, depression, and other CNS disorders.

The particle size of the nanoparticle dispersion can be measured using techniques such as light scattering with either water or a dilute surface stabilizer solution as the diluent. Measurements may be verified using microscopy. Particle size distributions may be determined using a Horiba 950 particle size analyser as a wet suspension. The volume based particle size (Dv50) is expressed herein by the mean volume diameter of the particles. Particle size measurement can also be carried out using PCS (Dynamic light scattering measurements).

In an embodiment, the population of particles of aripiprazole lauroxil in $AL_{NCD}$ has a volume-based particle distribution size (Dv50) of less than about 1000 nm. In an embodiment, the population of particles of aripiprazole lauroxil in $AL_{NCD}$ has a volume-based particle distribution size (Dv50) between about 175 nm and about 350 nm.

In an embodiment, the $AL_{NCD}$ has a ratio of particles to polysorbate 20 of between about 0.1:1 and about 40:1. In an embodiment, the $AL_{NCD}$ has a ratio of particles to polysorbate 20 of 17:1.

In an embodiment, the $AL_{NCD}$ comprises about 20-30 weight percent aripiprazole lauroxil, about 1-2 weight percent polysorbate 20, about 0.5-1 weight percent sodium citrate, 0.1-0.5 weight percent sodium chloride, and an aqueous buffer. In an embodiment, the $AL_{NCD}$ comprises about 26 weight percent aripiprazole lauroxil, about 1.53 weight percent polysorbate 20, about 0.76 weight percent sodium citrate, 0.31 weight percent sodium chloride, and an aqueous buffer.

In an embodiment, the $AL_{NCD}$ comprises about 26 weight percent aripiprazole lauroxil particles, about 1.53 weight percent polysorbate 20, about 0.76 weight percent sodium citrate, 0.31 weight percent sodium chloride, and an aqueous buffer; wherein the particles of aripiprazole lauroxil have a volume-based particle distribution size (Dv50) between about 175 nm and about 350 nm.

Treatment Methods

The methods and dosing regimens provided herein can be used for the treatment of a variety of disorders in a subject in need thereof. For example, the pharmaceutical compositions described herein can be used to treat subjects with depression, schizophrenia, and bipolar disorder.

In an aspect, provided herein is a method of treating these disorders, e.g., schizophrenia, in a subject in need thereof, the method comprising administering to the subject:
 a first component comprising aripiprazole;
 a second component comprising $AL_{NCD}$; and
 a third component comprising a therapeutically effective amount of aripiprazole lauroxil.

In an aspect, provided herein is a method of treating schizophrenia in a subject in need thereof, the method comprising administering to the subject:
 a first component comprising about 5-50 mg of aripiprazole;
 a second component comprising about 629-695 mg of $AL_{NCD}$; and
 a third component comprising a therapeutically effective amount of aripiprazole lauroxil.

In another aspect, provided herein is a method of treating schizophrenia in a subject in need thereof, the method comprising administering to the subject:
 a first component comprising aripiprazole;
 a second component comprising $AL_{NCD}$; and
 a third component comprising aripiprazole lauroxil;

wherein the dosages of the first, second, and third components combined are sufficient to maintain a therapeutically effective mean blood plasma level of aripiprazole in the subject.

In an embodiment, the therapeutically effective mean blood plasma level of aripiprazole is about 102-435 ng/mL at steady-state plasma level. In another embodiment, the therapeutically effective mean blood plasma level of aripiprazole is greater than about 102 ng/mL at steady-state plasma level. In another embodiment, the therapeutically effective mean blood plasma level of aripiprazole is less than about 435 ng/mL at steady-state plasma level. In another embodiment, the therapeutically effective mean blood plasma level of aripiprazole is reached within 24 hours of the initial treatment. In another embodiment, the therapeutically effective mean blood plasma level of aripiprazole is maintained for no less than 21 days.

In an aspect, provided herein is a kit for the treatment of schizophrenia, wherein the kit comprises therapeutically effective amounts of:
 a first component comprising aripiprazole;
 a second component comprising $AL_{NCD}$; and
 a third component comprising aripiprazole lauroxil;
 and further comprises instructions for administration, wherein the instructions specify oral administration of the first component, intra-muscular administration of the second component, and intra-muscular administration of the third component.

In an embodiment, a therapeutically effective amount of the agent is given to a subject using the pharmaceutical compositions provided herein. The term "therapeutically effective amount" is further meant to define an amount resulting in the improvement of any parameters or clinical symptoms. The actual dose may vary with each patient and does not necessarily indicate a total elimination of all disease symptoms. In the case of antipsychotics, the management of exacerbations and maintenance of remission of psychiatric symptoms are main goals of therapy, and selection of the appropriate drug and dosage in a particular disease balances these goals with the minimization of adverse events attributable to the drug.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Administration/Dosage

Actual dosage levels of the components of the methods and dosing regimens provided herein can be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

Compounds of the methods and dosing regimens provided herein can be orally administered in an amount from about 10 mg to about 2000 mg (including e.g., about 10 mg to about 500 mg) per day in single or multiple doses. Thus, in an embodiment of the methods of treatment provided herein, the first component (aripiprazole) is administered at a dosage of about 5-50 mg per day. In a further embodiment, the first component (aripiprazole) is administered at a dosage of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg per day. In a further embodiment, the first component (aripiprazole) is administered at a dosage of about 5 mg, 10 mg, 15 mg, 20 mg, 25 mg, or 30 mg per day. In a further embodiment, the first component (aripiprazole) is administered at a dosage of about 30 mg per day. In yet another embodiment, the first component (aripiprazole) is administered at a dosage of about 15 mg per day over two days. In still another embodiment, the first component (aripiprazole) is administered at a dosage of about 10 mg per day over three days.

Compounds of the methods and dosing regimens provided herein can be intra-muscularly administered in an amount from about 10 mg to about 2000 mg (including e.g., about 10 mg to about 500 mg) per day in single or multiple doses. Thus, in an embodiment of the methods of treatment provided herein, the second component ($AL_{NCD}$) is administered at a dosage of about 629-695 mg per day. In a further embodiment, the second component ($AL_{NCD}$) is administered at a dosage of about 630 mg, 640 mg, 650 mg, 660 mg, 662 mg, 670 mg, 675 mg, 677 mg, 680 mg, 690 mg, or 700 mg per day. In a further embodiment, the second component ($AL_{NCD}$) is administered at a dosage of about 675 mg per day. In another embodiment, the second component ($AL_{NCD}$) is administered at a dosage of about 677 mg per day.

Compounds of the methods and dosing regimens provided herein can be intra-muscularly administered in an amount from about 10 mg to about 2000 mg (including, e.g., about 300 mg to about 1500 mg or about 629 to about 695 mg) per day in single or multiple doses. Thus, in an embodiment of the methods of treatment provided herein, the third component (aripiprazole lauroxil) is administered at a dosage of about 300-1500 mg per day. In a further embodiment, the third component (aripiprazole lauroxil) is administered at a dosage of about 441 mg, 662 mg, 882 mg, or 1064 mg per day.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of anxiety, depression, bipolar disorder, autism-related irritability, and psychotic conditions including acute mania, schizophrenia, and schizophreniform disorder in a patient.

In one embodiment, the components of the methods and dosing regimens provided herein are formulated using one or more pharmaceutically acceptable excipients or carriers. In one embodiment, the pharmaceutical compositions of the invention comprise a therapeutically effective amount of a disclosed compound and a pharmaceutically acceptable carrier.

Herein, a reference to a "dose" or "dosage" is to a dose of the active agent. For example, "a second component comprising about 629-695 mg of $AL_{NCD}$" refers to an amount of $AL_N$co that comprises 629-695 mg of aripipraxzole lauroxil. As discussed above, the aripiprazole and/or aripipraxzole lauroxil components can be pharmaceutical compositions comprising the active agent and a pharmaceutically acceptable carrier. Any reference to a "dose" or "dosage" of these components refers to a dose or dosage of the active agent (aripiprazole and/or aripipraxzole lauroxil, irrespective of the pharmaceutically acceptable carrier).

In an embodiment, the active agent in the first component is aripiprazole. In another embodiment, the active agent in the second component is aripiprazole lauroxil. In yet another embodiment, the active agent in the third component is aripiprazole.

Different dosage regimens may be used to treat schizophrenia. In some embodiments, a daily dosage, such as any of the exemplary dosages described above, is administered once, twice, three times, or four times a day for three, four, five, six, seven, eight, nine, or ten days. In an embodiment, the method comprises a regimen wherein the first, second, and third components are administered at substantially the same time.

In an embodiment, the dosage of the first component is administered over the first three days of treatment. In an embodiment, the first component is administered over the first two days of treatment. In an embodiment, the first component is administered only on the first day of treatment. In an embodiment, the first component is only administered once during the treatment duration. In an embodiment, the first component is not administered again within 21 days following the initial treatment.

In an embodiment, the first, second, and third components are administered at substantially the same time, and wherein the first component is not administered again within 21 days of the initial administration.

In an embodiment, the first, second, and third components are administered at substantially the same time, followed by a second treatment comprising administering the third component alone.

In an embodiment, the second treatment occurs no earlier than 21 days after the initial treatment.

In an embodiment, the method comprises a regimen wherein the first component is only administered on the first and/or second days of treatment, the second component is only administered on the first day of treatment, and the third component is administered once within the first 10 days of treatment. In another embodiment, the regimen further comprises a second administration of the third component alone. In yet another embodiment, the third component is administered on the first day of treatment. In still another embodiment, the third component is administered on the second day of treatment. In an embodiment, the third component is administered 7-10 days after the start of the treatment regimen. In an embodiment, the third component is administered 3-6 days after the start of the treatment regimen. In another embodiment, the first component is only administered on the first and second day of treatment. In yet another embodiment, the first component is only administered on the first day of treatment.

In an embodiment, the method comprises a regimen wherein the first component is only administered on the first and second days of treatment at a dosage of 15 mg per day, the second component is only administered on the first day of treatment, and the third component is administered in the second day of treatment.

In an embodiment, the method comprises a regimen wherein the first component is only administered on the first day of treatment, the second component is only administered on the first day of treatment, and the third component is administered 7-10 days after the start of the treatment regimen. In still another embodiment, the third component is administered 7, 8, 9, or 10 days after the start of the treatment regimen. In yet another embodiment, the third component is administered 7 days after the start of the treatment regimen. In still another embodiment, the third component is administered 8 days after the start of the treatment regimen. In an embodiment, the third component is administered 9 days after the start of the treatment regimen. In another embodiment, the third component is administered 10 days after the start of the treatment regimen.

In an embodiment, the method comprises a regimen wherein the first component is only administered on the first day of treatment, the second component is only administered on the first day of treatment, and the third component is administered 3-6 days after the start of the treatment regimen. In still another embodiment, the third component is administered 3, 4, 5, or 6 days after the start of the treatment regimen. In yet another embodiment, the third component is administered 3 days after the start of the treatment regimen. In still another embodiment, the third component is administered 4 days after the start of the treatment regimen. In an embodiment, the third component is administered 5 days after the start of the treatment regimen. In another embodiment, the third component is administered 6 days after the start of the treatment regimen.

Routes of administration of any of the compositions of the invention include oral, nasal, rectal, intravaginal, parenteral, buccal, sublingual or topical. The compounds for use in the methods and dosing regimens provided herein may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

In an embodiment, the preferred route of administration for the first component (aripiprazole) is oral.

In an embodiment, the preferred route of administration for the second component ($AL_{NCD}$) is intra-muscular. In a further embodiment, the preferred route of administration for the second component ($AL_{NCD}$) is intra-muscular to the deltoid or the gluteus. In a further embodiment, the preferred route of administration for the second component ($AL_{NCD}$) is intra-muscular to the deltoid.

In an embodiment, the preferred route of administration for the third component (aripiprazole lauroxil) is intra-muscular. In a further embodiment, the preferred route of administration for the third component (aripiprazole lauroxil) is intra-muscular to the deltoid or the gluteus.

In an embodiment, the route of administration for the first component (aripiprazole) is oral, the route of administration for the second component ($AL_{NCD}$) is intra-muscular, and the route of administration for the third component (aripiprazole lauroxil) is intra-muscular.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. The following examples further illustrate aspects of the present invention. However, they are in no way a limitation of the teachings or disclosure of the present invention as set forth

EXAMPLES

Example 1: Study Design and Treatment Regimen

The study was conducted in accordance with the Declaration of Helsinki, and Good Clinical Practice Guidelines agreed by the International Conference on Harmonization, 1997. The study protocols, amendments, and informed consent forms were approved by an independent ethics committee/institutional review board for each site. All patients provided written informed consent before entering the study.

As used herein, $AL_{NCD}$ refers to a pharmaceutical composition comprising about 26 weight percent aripiprazole lauroxil particles, about 1.53 weight percent polysorbate 20, about 0.76 weight percent sodium citrate, 0.31 weight percent sodium chloride, and an aqueous buffer; wherein the particles of aripiprazole lauroxil have a volume-based particle distribution size (Dv50) between about 175 nm and about 350 nm.

This was a phase 1, double-blind, placebo-controlled study to assess the PK, safety, and tolerability of two initiation regimens for starting treatment with AL in patients with schizophrenia. The first regimen was a 1-day initiation regimen comprising a single 662 mg $AL_{NCD}$ dose along with a single dose of 30 mg oral aripiprazole. The second regimen was a 21-day oral initiation regimen that was based on the regimen used in the pivotal 12-week phase 3 study of AL. In this phase 1 study, the 1-day initiation regimen was compared with the 21-day initiation regimen (starting AL 441 or 882 mg along with 21 days of 15 mg oral aripiprazole).

Figure 1:
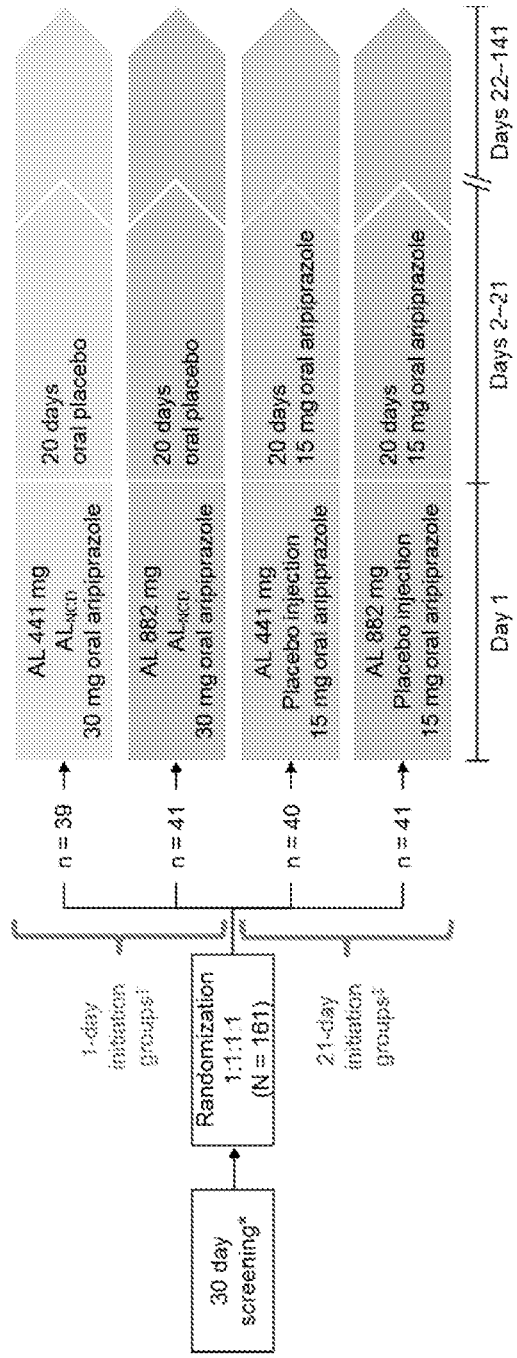
FIG. 1: Study design from Example 1.

The duration of the study was approximately 6 months and consisted of screening, inpatient dosing, outpatient, and follow-up period (FIG. 1). Prospective patients were evaluated during a 30-day screening period prior to dosing, and during this time, patients that had never received aripiprazole were administered a 5 mg test dose 30 and 29 days prior to entering the study. A total of 160 patients were planned to be enrolled and randomized 1:1:1:1 to one of four treatment groups, as follows: 1-day initiation regimen groups (30 mg oral aripiprazole plus $AL_{NCD}$, plus either AL 441 or 882 mg [on day 1] then 20 days of oral placebo), or 21-day initiation regimen groups (15 mg oral aripiprazole plus placebo IM, plus either AL 441 or 882 mg [on day 1] followed by 20 days of oral aripiprazole 15 mg/day). In all study groups, the order of administration on day 1 was as follows: first, oral aripiprazole; second, IM injection of $AL_{NCD}$ or placebo (administered no more than 15 minutes after oral aripiprazole); third, IM injection of AL (administered no more than 30 minutes after IM injection of $AL_{NCD}$ or placebo). $AL_{NCD}$ or placebo were administered as IM injections in the gluteal muscle. For the AL doses, a single 441 mg dose was given in the deltoid muscle or a single 882 mg dose in the gluteal muscle contralateral to the $AL_{NCD}$ (or placebo) injection.

Patients were admitted as inpatients 1 day prior to their first scheduled dose and were maintained as inpatients for the first 15 days. Following discharge, patients returned for 17 outpatient follow-up assessments, with the last assessment on day 141. PK samples were taken daily on days 1-15, every other day from days 17-25, on days 28 and 31, once-weekly from days 35 to 85, and on days 113 and 141. On days 1 and 21, samples were collected at multiple time points (as detailed in Example 3).

Example 2: Study Population

Eligible patients were adults aged 18-65 years with a diagnosis of chronic schizophrenia or schizoaffective disorder based on *The Diagnostic and Statistical Manual of Mental Disorders, Fifth Edition* (DSM-5) and a documented history of tolerability to aripiprazole or demonstrated tolerability to test doses during screening. In this study, patients were required to be clinically stable, defined as having no hospitalizations for acute psychiatric exacerbations within ≤3 months prior to screening and having a Clinical Global Impressions-Severity (CGI-S) score of at screening and study initiation. Patients were on a stable oral antipsychotic medication regimen (excluding aripiprazole and clozapine) for months prior to screening without any medication changes between screening and randomization.

Key exclusion criteria included patients who had received oral aripiprazole ≤28 days prior to randomization or any other LAI antipsychotic months prior to admission and patients who were currently or who had participated in a clinical trial involving any investigational product ≤3 months prior to admission. Patients who had received AL or IM depot aripiprazole ≤6 months prior to inpatient admission were excluded. A history of primary psychopathology other than schizophrenia or schizoaffective disorder, CYP2D6 poor metabolizer status, or a positive test for illicit drug use either at screening or admission were not permitted.

Example 3: Study Assessments

Blood samples for liquid chromatography-tandem mass spectrometry were collected for analysis of aripiprazole plasma concentrations. Samples were collected within 1 hour pre-dose and 1, 2, 3, 4, 5, 6, and 8 hours (±15 minutes) post-dose on day 1. On post-initiation days 2-20, a single sample was collected prior to oral aripiprazole (or oral placebo) administration. As on day 1, following collection of the pre-dose sample on day 21, additional samples were collected 1, 2, 3, 4, 5, 6, and 8 hours (±15 minutes) post-dose. For days 23-85, a single sample was collected within ±2 hours of the day 1 oral dosing time or as close to that timeframe as possible. Single PK samples were collected on day 113 and day 141.

All safety analyses were performed using observed data from the safety population, and measurements included adverse events (AEs), vital signs measurements, weight, laboratory test results, ECG findings, Columbia-Suicide Severity Rating Scale (C-SSRS) responses, movement disorder measures, CGI-S responses, and injection-site evaluation.

AEs were assessed daily on days 1-15, every other day from days 17-25, on days 28 and 31, once-weekly from days 35 to 85, and on days 113 and 141. Injection-site evaluations were carried out daily on days 1-15, every other day from days 17-25, and on day 28. The injection site and surrounding area were evaluated with each injection (separately for the $AL_{NCD}$ or placebo injection site and AL site). Any observed injection-site reactions were followed until resolution.

Example 4: Statistical Analysis

Study populations consisted of the safety population (all patients that received the study drug), and the PK population (all patients who received study drug and had ≥1 measurable concentration of aripiprazole).

The AUC calculated from day 0 to 28 days ($AUC_{0-28}$) was computed using the linear trapezoidal rule and included only oral pre-dose concentrations collected on days 1 and 21. Actual elapsed time from dosing was used to estimate individual parameters. Additionally, the proportion of patients to reach known therapeutic concentrations of aripiprazole within 4 days after AL initiation was calculated. The 1-day initiation regimen was designed to achieve therapeutic concentrations within 4 days, consistent with the oral initiation regimen indicated in the AL prescribing information. Aripiprazole concentrations and $AUC_{0-28}$ were summarized descriptively.

A post-hoc evaluation comparing aripiprazole concentrations results from the present study with observed concentrations from the 12-week phase 3 efficacy study (that used the 21-day oral regimen) was carried out.

Safety and tolerability parameters were estimated in the safety population. AEs that were newly occurring or worsened from the time of administration of the first dose of study drug ($AL_{NCD}$ and a single 30 mg oral aripiprazole dose or placebo injection and 21 days of oral aripiprazole 15 mg, plus either AL 441 or 882 mg) were summarized using descriptive statistics.

Example 5: Patient Disposition and Baseline Characteristics

In total, 161 patients were enrolled, received one of the initiation regimens, and were included in the PK and safety populations (Table 1). Patients were randomized to receive a 1-day initiation regimen (n=80) or a 21-day initiation regimen (n=81), along with an AL starting dose of either 441 or 882 mg. In total, 39 patients were enrolled in the AL 441 mg/1-day initiation group and 41 patients were enrolled in the AL 882 mg/1-day initiation group. Of those enrolled in the 21-day initiation regimen groups, 40 patients were assigned to the AL 441 mg/21-day initiation group and 41 patients were assigned to the AL 882 mg/21-day initiation group.

A total of 133 (82.6%) patients completed the study. Among the 28 patients (17.4%) that did not complete the study, the reasons for study withdrawal were loss to follow-up and withdrawal by the patient (n=10, 6.2% each), AE (n=5, 3.1%), protocol deviation (n=2, 1.2%), and non-compliance with medication (n=1, 0.6%).

Patient demographics are summarized in Table 1. The mean age and BMI of the patients was 44 years and 29.5 $kg/m^2$, respectively. Overall, the treatment groups were generally well balanced for demographic and baseline characteristics.

TABLE 1

Patient Baseline Characteristics

| | | 1-day initiation regimen | | 21-day initiation regimen | |
|---|---|---|---|---|---|
| | | $AL_{NCD}$ | $AL_{NCD}$ | | |
| Parameter | All | initiation regimen + AL 441 mg[a] | initiation regimen + AL 882 mg[b] | 21-day initiation + AL 441 mg[c] | 21-day initiation + AL 882 mg[d] |
| n | 161 | 39 | 41 | 40 | 41 |
| Mean age, years (SD) | 44.0 (10.6) | 44.4 (10.0) | 42.3 (12.4) | 44.2 (9.7) | 45.0 (10.2) |
| Male, n (%) | 118 (73.3) | 30 (76.9) | 29 (70.7) | 27 (67.5) | 32 (78.0) |
| Race, n (%) | | | | | |
| Black or African-American | 125 (77.6) | 31 (79.5) | 33 (80.5) | 26 (65.0) | 35 (85.4) |
| White | 35 (21.7) | 8 (20.5) | 8 (19.5) | 14 (35.0) | 5 (12.2) |
| Asian | 1 (0.6) | 0 (0.0) | 0 (0.0) | 0 (0.0) | 1 (2.4) |
| Mean BMI, $kg/m^2$ (SD) | 29.5 (5.4) | 28.16 (5.5) | 29.8 (4.7) | 30.3 (5.3) | 29.7 (5.9) |
| Metabolizer status, n (%)[e] | | | | | |
| Extensive | 106 (65.8) | 26 (66.7) | 29 (70.7) | 25 (62.5) | 26 (63.4) |
| Intermediate | 51 (31.7) | 13 (33.3) | 10 (24.4) | 13 (32.5) | 15 (36.6) |
| Inconclusive | 4 (2.5) | 0 (0.0) | 2 (4.9) | 2 (5.0) | 0 (0.0) |

All values are mean values, unless otherwise indicated
AL aripiprazole lauroxil,
BMI body-mass index,
SD standard deviation
[a] 30 mg oral aripiprazole plus $AL_{NCD}$ (gluteal) plus AL 441 mg (deltoid) on day 1 followed by oral placebo for 20 days
[b] 30 mg oral aripiprazole plus $AL_{NCD}$ (gluteal) plus AL 882 mg (contralateral gluteal) on day 1 followed by oral placebo for 20 days
[c] 15 mg oral aripiprazole plus placebo injection (gluteal) plus AL 441 mg (deltoid) on day 1 followed by 20 days of 15 mg oral aripiprazole
[d] 15 mg oral aripiprazole plus placebo injection (gluteal) plus AL 882 mg (contralateral gluteal) on day 1 followed by 20 days of 15 mg oral aripiprazole
[e] Based on CYP2D6 analysis

Example 6: Pharmacokinetic Results

Figure 2:
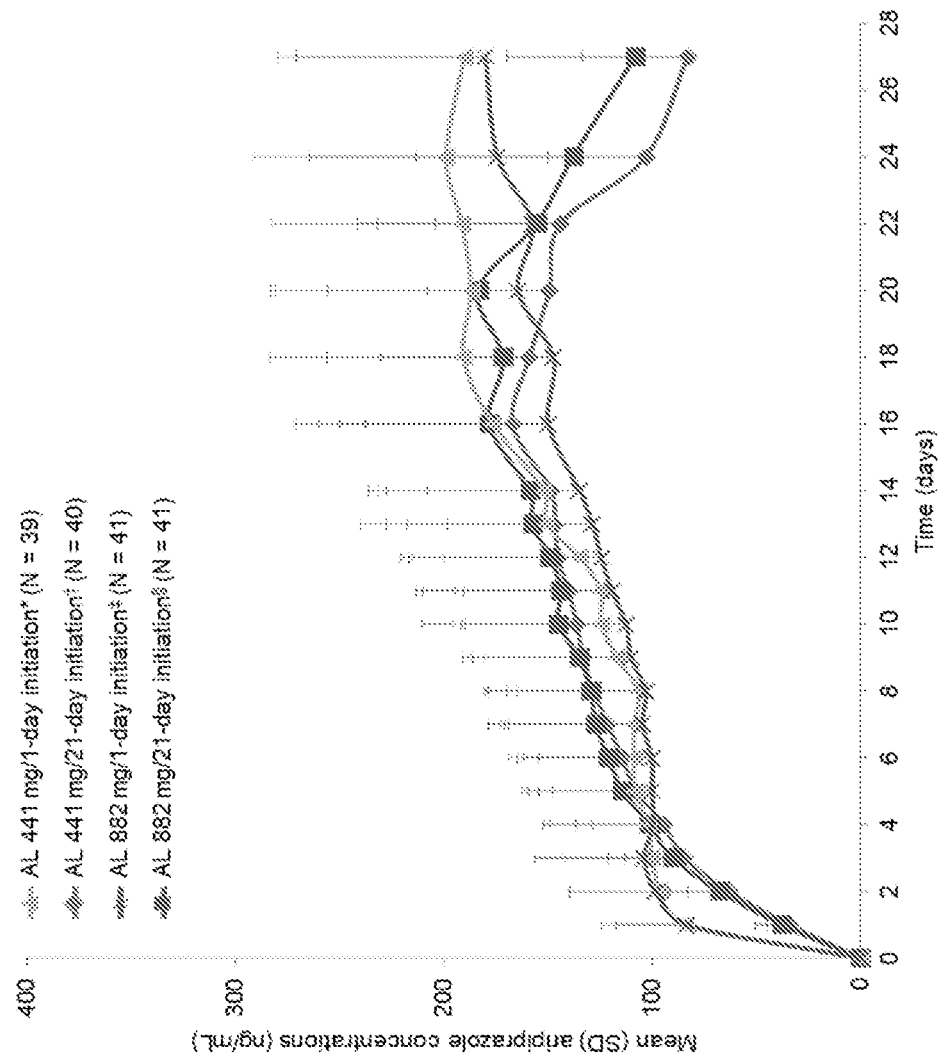
FIG. 2: Mean (SD) aripiprazole concentrations over time (28 days) following treatment initiation with oral aripiprazole (15 mg/day over 21 days) or $AL_{NCD}$ plus a single dose of oral aripiprazole (30 mg on day 1).

Results from the 1-day initiation regimen groups showed mean plasma aripiprazole concentrations and exposures within the first month that were comparable to the 21-day initiation regimen groups (FIG. 2). In the first 24 hours after initiation, higher aripiprazole concentrations were observed with the 1-day initiation regimen groups compared with the 21-day initiation regimen groups due to the higher dose of aripiprazole administered on day 1 with the 1-day initiation regimen (30 mg versus 15 mg). The plasma concentrations of post-initiation day 4 were of particular interest because the 1-day initiation regimen was designed to replicate the 21-day initiation regimen in achieving therapeutic aripiprazole concentrations within 4 days after the first AL dose. As shown in FIG. 2, the 1-day regimen results in achievement of therapeutic levels of aripiprazole, similar to the 21-day initiation regimen, within 4 days.

Figure 6A:
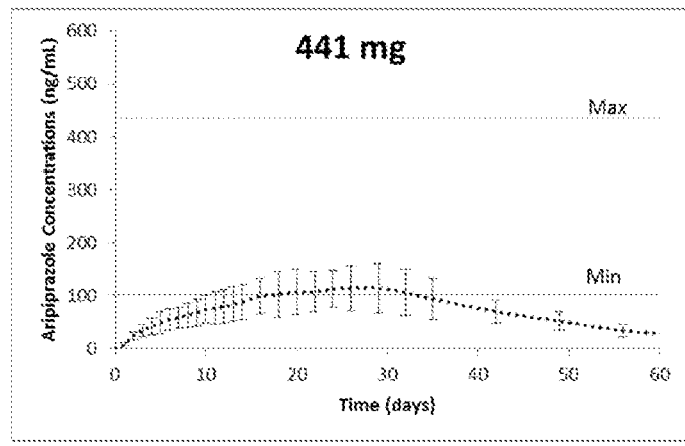
FIG. 6A: Mean aripiprazole concentrations following a single injection of $AL_{NCD}$ at the 441 mg dose relative to minimum and maximum thresholds established by the FDA.
Figure 6B:
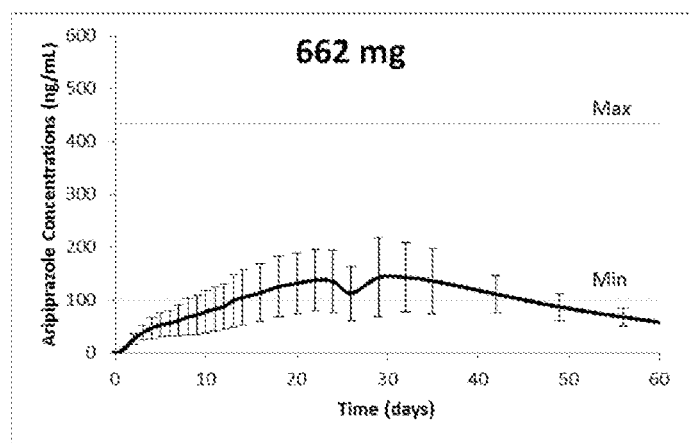
FIG. 6B: Mean aripiprazole concentrations following a single injection of $AL_{NCD}$ at the 662 mg dose relative to minimum and maximum thresholds established by the FDA.
Figure 6C:
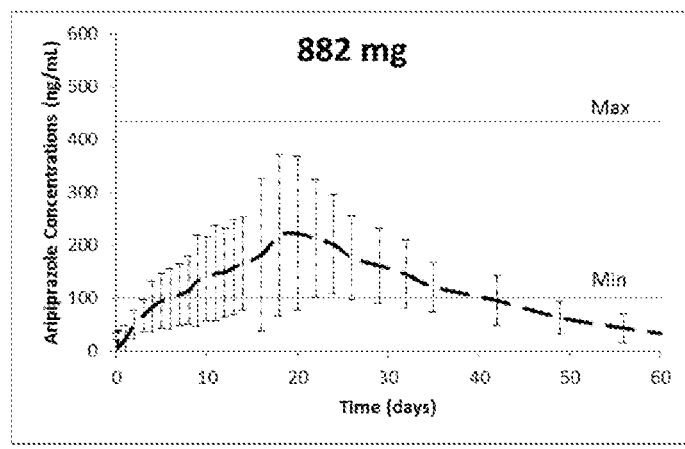
FIG. 6C: Mean aripiprazole concentrations following a single injection of $AL_{NCD}$ at the 882 mg dose relative to minimum and maximum thresholds established by the FDA.

As seen in FIG. 2, mean concentrations appear visually lower in the 1-day initiation regimen groups than in the 21-day initiation regimen groups from approximately day 4 to day 14, the error bars around the plasma concentration means show complete overlap in the range of concentrations across the treatment groups. As expected for the 21-day oral initiation regimen group, aripiprazole concentrations declined after day 21 upon discontinuation of the active oral medication. In contrast, for the 1-day initiation regimen groups, plasma aripiprazole concentrations did not show any meaningful changes until after post-initiation day 30 when mean aripiprazole concentrations began to decline (FIG. 6A, FIG. 6B, FIG. 6C). Indicating that the 1-day initiation regimen provides continuous coverage over a longer period compared with the 21-day initiation regimen.

Figure 3:
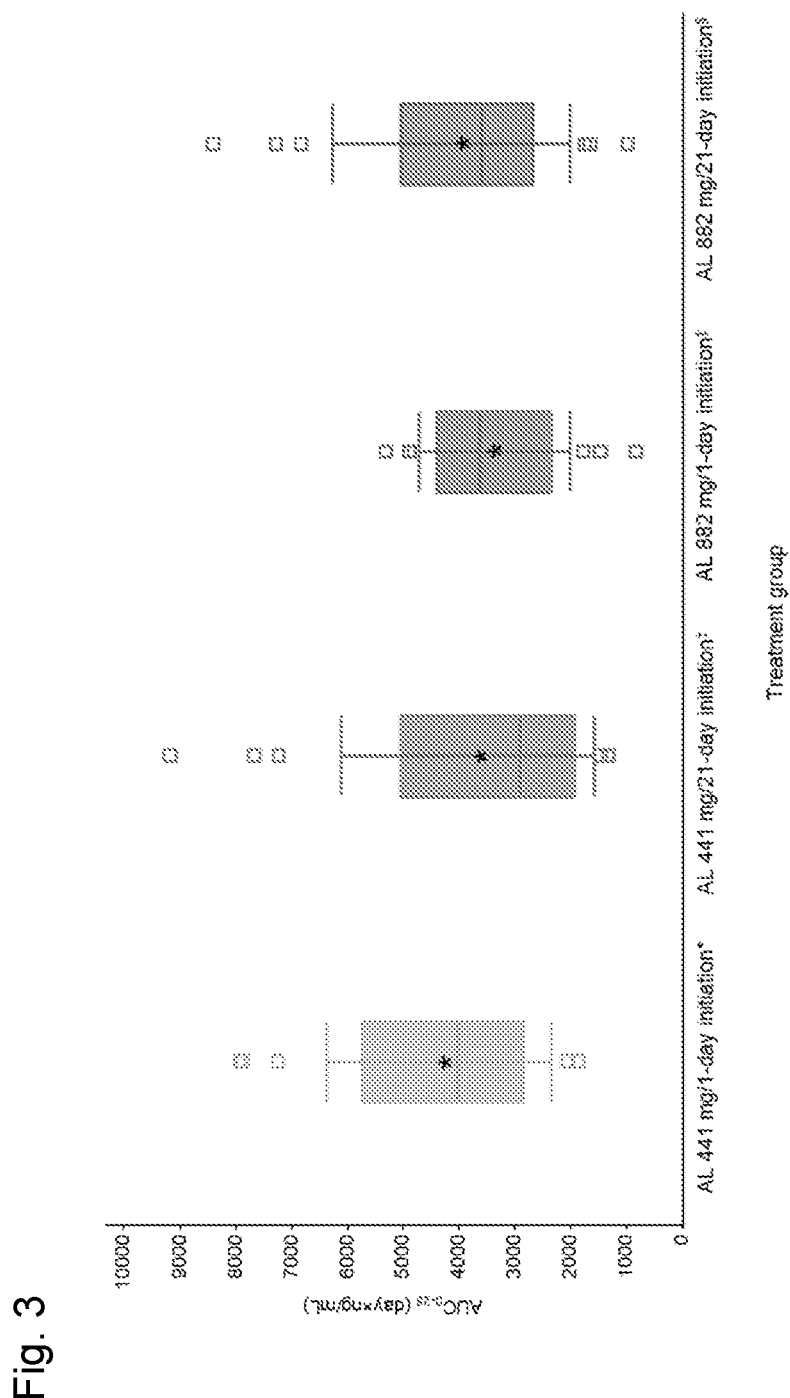
FIG. 3: Box plot of $AUC_{0-28}$ for aripiprazole, by starting AL dose/initiation regimen.

Values of $AUC_{0-28}$ were comparable across the four treatment groups (FIG. 3, Table 2). A comparison of the range of values across groups indicated similar exposure within the first month of treatment regardless of the initiation regimen used.

In the AL 441 mg/1-day initiation and AL 882 mg/1-day initiation groups, 26 patients (66.7%) and 28 patients (68.3%) experienced AEs, respectively, and 24 patients (60.0%) and 28 patients (68.3%) in the AL 441 mg and AL 882 mg/21-day initiation groups experienced AEs, respectively (Table 4). The majority of AEs were mild or moderate in intensity. Serious AEs were reported in six patients; three each in the 1-day initiation regimen (road traffic accident, status epilepticus, psychotic disorder, and schizoaffective disorder) and the 21-day initiation regimen groups (upper gastrointestinal haemorrhage, cellulitis, road traffic accident, and accidental overdose). Of these, schizoaffective disorder and status epilepticus were assessed as "possibly related" to treatment. A total of five patients discontinued the study due to AEs; three in the 1-day initiation regimen (road traffic accident, extrapyramidal disorder, and status epilepticus) and two in the 21-day initiation regimen (road traffic accident and nausea). One patient in the 21-day initiation regimen group died as a result of injuries sustained in a road traffic accident (considered not related to study drug). Overall, the most common AEs reported were injection-site pain (23.0%), headache (9.9%), weight increased (7.5%), insomnia (6.2%), dyspepsia (5.6%), and anxiety (5.0%). All other AEs occurred at an overall incidence of <5%.

ISRs and akathisia are considered AEs of special interest as they have been associated with the initiation of AL in previous studies. See, e.g., Meltzer, H. Y., et al., *J. Clin. Psychiatry*, 2015, 76(8), 1085-1090; McEvoy, J. P., et al., *J. Clin. Psychiatry*, 2017, 78(8), 1103-1109.

TABLE 2

$AUC_{0-28}$ data for aripiprazole, by starting AL dose/initiation regimen

| Treatment group | $AL_{NCD}$ initiation regimen + AL 441 mg* | 21-day oral initiation + AL 441 mg† | $AL_{NCD}$ initiation regimen + AL 882 mg‡ | 21-day oral initiation + AL 882 mg§ |
|---|---|---|---|---|
| N‖ | 37 | 39 | 39 | 39 |
| | | $Auc_{0-28}$ (day × ng/mL) | | |
| Mean (SD) | 4256.4 (1703.6) | 3371.6 (1110.5) | 3570.7 (1935.3) | 3911.9 (1661.6) |
| Range | 1854.8-7930.1 | 836.2-5320.3 | 1314.7-9179.2 | 978.8-8409.3 |

AL aripiprazole lauroxil,
$AUC_{0-28}$ area under the concentration-time curve from time zero until day 28,
SD standard deviation;
*AL 441 mg/1-day initiation: $AL_{NCD}$ intramuscular (gluteal) plus 30 mg oral aripiprazole plus intramuscular AL 441 mg (deltoid) on day 1 followed by 20 days of oral placebo;
†AL 882 mg/1-day initiation: $AL_{NCD}$ intramuscular (gluteal) plus 30 mg oral aripiprazole plus intramuscular AL 882 mg (contralateral gluteal) on day 1 followed by 20 days of oral placebo;
‡AL 441 mg/21-day initiation: placebo intramuscular (gluteal) plus 15 mg oral aripiprazole plus intramuscular AL 441 mg (deltoid) on day 1 followed by 20 days of 15 mg oral aripiprazole;
§AL 882 mg/21-day initiation: placebo intramuscular (gluteal) plus 15 mg oral aripiprazole plus intramuscular AL 882 mg (contralateral gluteal) on day 1 followed by 20 days of 15 mg oral aripiprazole;
‖$AUC_{0-28}$ values could not be estimated for all patients as some discontinued before day 28.

Figure 4:
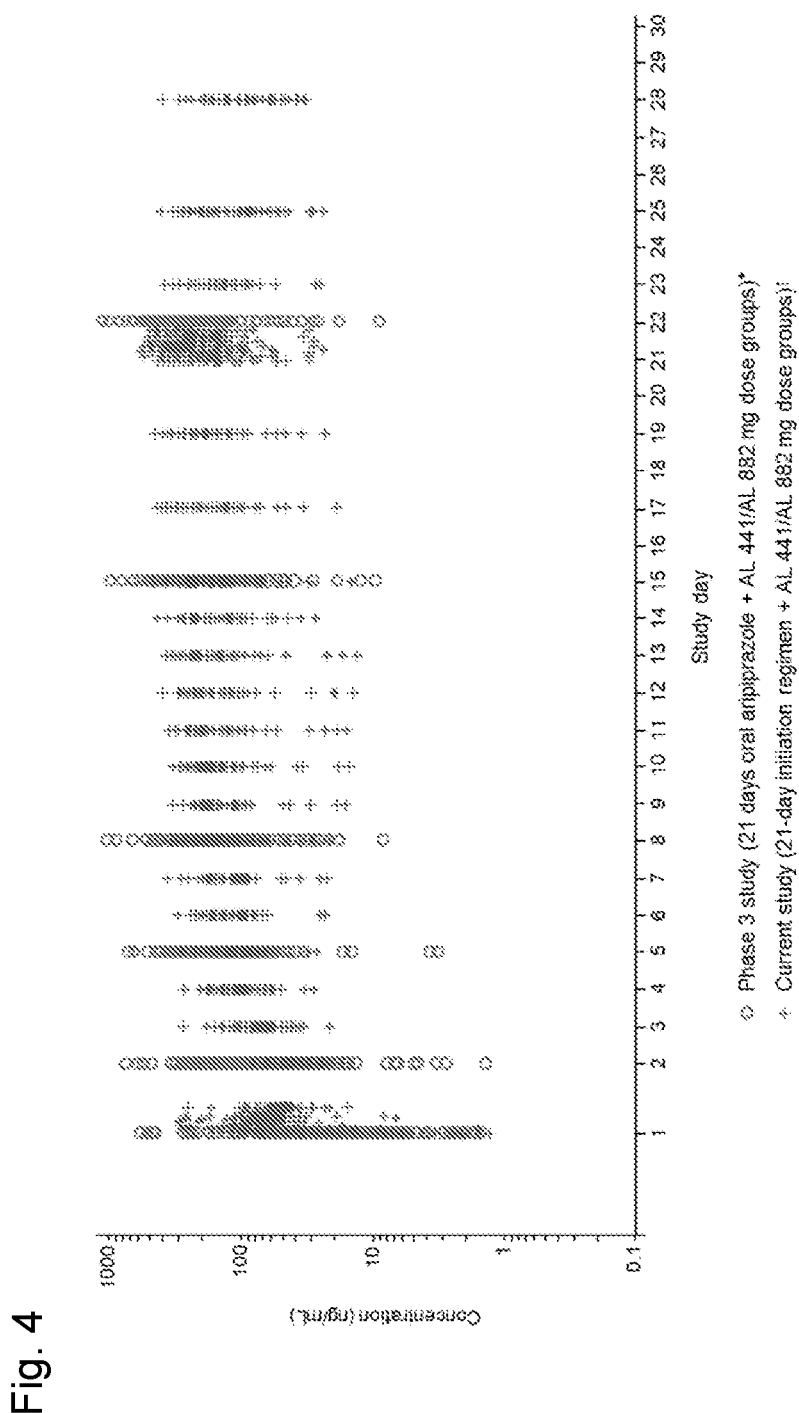
FIG. 4: Scatterplot of aripiprazole concentrations for patients receiving the 21-day initiation regimen in the phase 1 study (plus symbols) and the phase 3 efficacy study (circle symbols) for 441 mg and 882 mg AL dose groups combined (log scale).
Figure 5:
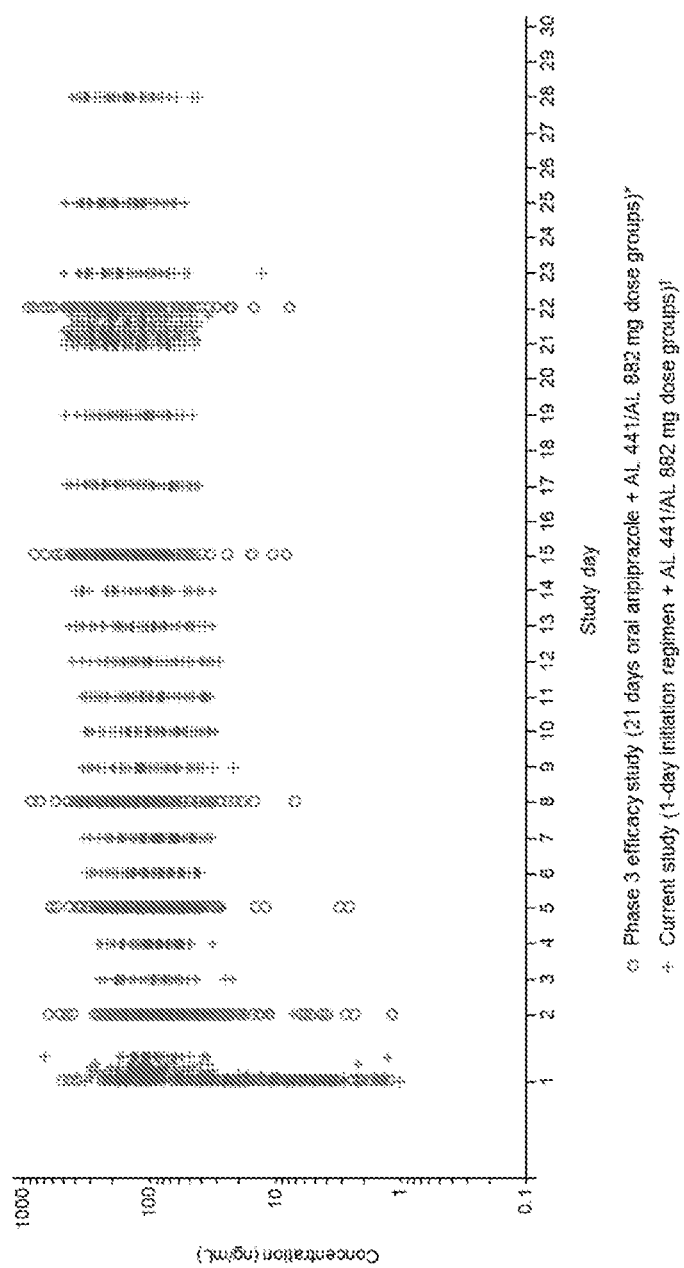
FIG. 5: Scatterplot of aripiprazole concentrations for patients receiving the 1-day initiation regimen in the phase 1 study (plus symbols) and the phase 3 efficacy study (circle symbols) for 441 mg and 882 mg AL dose groups combined (log scale).

A post-hoc comparison of aripiprazole concentrations resulting from the current study with those observed in the 12-week phase 3 efficacy study showed consistent and reproducible results across studies with the 21-day oral aripiprazole initiation regimen (FIG. 4). Importantly, the 1-day initiation regimen from the present study resulted in aripiprazole concentrations that were within the concentration range observed with the 21-day oral aripiprazole supplementation used in the phase 3 efficacy study (FIG. 5).

Example 7: Adverse Events Throughout the study period, small and similar mean changes (≤1.1) from baseline (score of 3.0; mild) in CGI-S score were seen in each initiation regimen group at all time points, indicating no change in disease severity. All patients had a score of 0 (no suicidal behavior or ideation) for C-SSRS throughout the study.

Overall, all Injection-Site Reactions (ISRs) associated with the $AL_N$co, placebo IM, AL 441 mg, and AL 882 mg injections were mild-to-moderate in severity.

In total, 14 out of 80 (17.5%) patients experienced ISRs associated with the $AL_{NCD}$ injection, compared with five out of 81 (6.2%) patients who received placebo injection (Table 3). The most common description of ISRs was injection-site pain, which was reported in 12 out of 80 (15.0%) patients who received $AL_{NCD}$ injection, compared with four out of 81 (4.9%) patients who received placebo IM injection. The incidence of injection-site pain associated with $AL_{NCD}$ was similar whether patients received AL injections in the deltoid muscle (AL 441 mg; n=7, 17.5%) or in the contralateral gluteal muscle (AL 882 mg; n=5, 12.5%).

In total, 18 out of 79 (22.8%) patients who received AL 441 mg in the deltoid muscle and 15 out of 82 (18.3%)

patients who received AL 882 mg in the gluteal muscle experienced ISRs (Table 2). The most common description of ISRs was injection-site pain, which was reported in 16 out of 79 (20.3%) and 15 out of 82 (18.3%) patients who received AL 441 mg and AL 882 mg, respectively.

as having mild akathisia definitely related to the study drug. The other two patients experienced akathisia in the third week of treatment. One these was rated mild and the other moderate in severity, assessed as "probably related" and

TABLE 3

Injection-site reactions by treatment group associated with $AL_{NCD}$ or placebo injection, and those associated with aripiprazole lauroxil (441 mg or 882 mg)

| Injection | $AL_{NCD}{}^a$ (n = 80), n (%) | Placebo injection[b] (n = 81), n (%) | AL 441 mg[c] (n = 79), n (%) | AL 882 mg[d] (n = 82), n (%) |
|---|---|---|---|---|
| Patients with at least one ISR[e] | 14 (17.5) | 5 (6.2) | 18 (22.8) | 15 (18.3) |
| Injection-site pain | 12 (15.0) | 4 (4.9) | 16 (20.3) | 15 (18.3) |
| Injection-site induration | 3 (3.8) | 0 | 4 (5.1) | 2 (2.4) |
| Injection-site swelling | 0 | 0 | 2 (2.5) | 1 (1.2) |
| Injection-site discomfort | 0 | 0 | 1 (1.3) | 0 |
| Injection-site erythema | 1 (1.3) | 1 (1.2) | 1 (1.3) | 0 |

The injection site and surrounding area were evaluated with each injection (separately for the $AL_{NCD}$ or placebo injection site and AL site). Any observed injection site reactions were followed until resolution
AL aripiprazole lauroxil,
$AL_{NCD}$ aripiprazole lauroxil Nanoparticle dispersion,
ISR injection-site reaction
[a] Patients received a single $AL_{NCD}$ injection (gluteal) on day 1 as part of the 1-day initiation regimen
[b] Patients received a placebo injection (gluteal) on day 1 as part of the 21-day initiation regimen
[c] Patients received an AL 441 mg injection (deltoid) on day 1 as part of the 1-day or 21-day initiation regimens
[d] Patients received an AL 882 mg injection (contralateral gluteal) on day 1 as part of the 1-day or 21-day initiation regimen
[e] A single patient could have more than one injection-site reaction The overall incidence of akathisia in all groups was low, with a total AE rate of six patients out of 140 (3.7%). Among patients treated with 1-day initiation regimen, akathisia was reported in four out of 80 patients (5%). Two of these patients reported mild akathisia during the first week of treatment, with one of the patients assessed as having mild akathisia probably not related to the study drug and the other as having mild akathisia definitely related to the study drug. The other two patients experienced akathisia in the third week of treatment. One these was rated mild and the other moderate in severity, assessed as "probably related" and "definitely related" to treatment, respectively. Among patients treated with the 21-day oral regimen, mild akathisia was reported in two out of 81 patients (2.5%). One experienced the first akathisia event in the second week and the other in the third week of treatment, assessed as "possibly" and "probably related" to treatment, respectively.

TABLE 4

Adverse events in ≥2 patients

| | 1-day initiation/AL 441 mg[a] n (%) | 1-day initiation/AL 882 mg[b] n (%) | 21-day initiation/AL 441 mg[c] n (%) | 21-day initiation/AL 882 mg[d] n (%) |
|---|---|---|---|---|
| N | 39 | 41 | 40 | 41 |
| Any AE | 26 (66.7) | 28 (68.3) | 24 (60.0) | 28 (68.3) |
| Gastrointestinal disorders | 9 (23.1) | 4 (9.8) | 6 (15.0) | 8 (19.5) |
| Dyspepsia | 3 (7.7) | 2 (4.9) | 1 (2.5) | 3 (7.3) |
| Diarrhea | 1 (2.6) | 2 (4.9) | 1 (2.5) | 1 (2.4) |
| Toothache | 1 (2.6) | 0 | 3 (7.5) | 1 (2.4) |
| Nausea | 2 (5.1) | 0 | 0 | 2 (4.9) |
| Vomiting | 0 | 2 (4.9) | 1 (2.5) | 1 (2.4) |
| General disorders and administration site conditions[e] | 10 (25.6) | 9 (22.0) | 14 (35.0) | 10 (24.4) |
| Injection site pain | 9 (23.1) | 8 (19.5) | 11 (27.5) | 9 (22.0) |
| Injection site induration | 2 (5.1) | 2 (4.9) | 2 (5.0) | 1 (2.4) |
| Fatigue | 0 | 1 (2.4) | 2 (5.0) | 1 (2.4) |
| Injection site swelling | 0 | 0 | 2 (5.0) | 1 (2.4) |
| Immune system disorders | 0 | 3 (7.3) | 1 (2.5) | 0 |
| Asthma | 0 | 2 (4.9) | 0 | 0 |
| Infections and infestations | 3 (7.7) | 7 (17.1) | 5 (12.5) | 5 (12.2) |
| URTI | 0 | 2 (4.9) | 2 (5.0) | 3 (7.3) |
| Nasopharyngitis | 1 (2.6) | 2 (4.9) | 0 | 2 (4.9) |
| Injury, poisoning, and procedural complications | 2 (5.1) | 2 (4.9) | 4 (10.0) | 3 (7.3) |
| Investigations | 6 (15.4) | 7 (17.1) | 4 (10.0) | 5 (12.2) |
| Weight increased | 5 (12.8) | 4 (9.8) | 2 (5.0) | 1 (2.4) |
| Weight decreased | 1 (2.6) | 2 (4.9) | 0 | 2 (4.9) |
| Musculoskeletal and connective tissue disorders | 4 (10.3) | 3 (7.3) | 3 (7.5) | 1 (2.4) |

TABLE 4-continued

Adverse events in ≥2 patients

|  | 1-day initiation/AL 441 mg[a] n (%) | 1-day initiation/AL 882 mg[b] n (%) | 21-day initiation/AL 441 mg[c] n (%) | 21-day initiation/AL 882 mg[d] n (%) |
|---|---|---|---|---|
| Musculoskeletal pain | 2 (5.1) | 0 | 1 (2.5) | 0 |
| Nervous system disorders | 8 (20.5) | 9 (22.0) | 6 (15.0) | 7 (17.1) |
| Headache | 3 (7.7) | 3 (7.3) | 5 (12.5) | 5 (12.2) |
| Akathisia | 1 (2.6) | 3 (7.3) | 0 | 2 (4.9) |
| Psychiatric disorders | 6 (15.4) | 5 (12.2) | 4 (10.0) | 5 (12.2) |
| Insomnia | 2 (5.1) | 2 (4.9) | 3 (7.5) | 3 (7.3) |
| Anxiety | 2 (5.1) | 4 (9.8) | 2 (5.0) | 0 |
| Respiratory, thoracic, and mediastinal disorders | 2 (5.1) | 2 (4.9) | 1 (2.5) | 1 (2.4) |
| Vascular disorders | 0 | 1 (2.4) | 0 | 3 (7.3) |
| Hypertension | 0 | 1 (2.4) | 0 | 3 (7.3) |

AE adverse event,
AL aripiprazole lauroxil,
URTI upper respiratory tract infections
[a]30 mg oral aripiprazole plus $AL_{NCD}$ (gluteal) plus AL 441 mg (deltoid) on day 1 followed by oral placebo for 20 days
[b]30 mg oral aripiprazole plus $AL_{NCD}$ (gluteal) plus AL 882 mg (contralateral gluteal) on day 1 followed by oral placebo for 20 days
[c]15 mg oral aripiprazole plus placebo injection (gluteal) plus AL 441 mg (deltoid) on day 1 followed by 20 days of 15 mg oral aripiprazole
[d]15 mg oral aripiprazole plus placebo injection (gluteal) plus AL 882 mg (contralateral gluteal) on day 1 followed by 20 days of 15 mg oral aripiprazole Example 8: Population Pharmacokinetic (PK) Model The PopPK model for aripiprazole was developed using data from four Phase 1 studies, three of which were critical to the formulation development and feasibility of using $AL_{NCD}$ as an initiation regimen for AL (Hard et al. CNS Drugs, submitted; Wehr et al. in preparation). These studies (ALK9072-1, ALK9072-B102 and ALK9072-B103) will be referred to here as Study 1, Study 2, and Study 3, respectively. The fourth study was a prior phase 1 study where AL was administered alone (ALKS9072-A105, referred to as Study 4). All the studies enrolled adult patients with schizophrenia or schizoaffective disorder that were stable on a first-line antipsychotic medication (excluding aripiprazole); all patients with sufficient data on dosing, actual sampling time, and aripiprazole concentration data were included in the PopPK analysis.

The mean patient age was 45.2±standard deviation (SD) 10.8 years; 73% were male, 78% were Black or African American, and the mean body weight was 89.1±17.9 kg (Table 1). A total of 12,768 plasma aripiprazole concentrations (including 351 [3%] records that were below the lower limit of quantitation) from 343 patients were included in the analysis. The dataset contained 2,536 dosing records (1,742 oral aripiprazole, 626 AL and 168 $AL_{NCD}$ doses).

The model was developed using non-linear mixed-effect modeling with NONMEM® program version 7.3.0 and PDx-Pop version 5.1 was used as the NONMEM interface (full details of the development of the PopPK model are provided in the Supplementary material). For modelling, doses of AL and $AL_{NCD}$ were expressed as aripiprazole equivalents of 75, 150, 300, 450, 600 and 724 mg (corresponding to $AL_{NCD}$ or AL doses of 110, 221, 441, 662, 882 and 1064 mg, respectively). A previously developed model for AL that included an oral input function served as the starting point for model development, which was expanded to include an input function for $AL_{NCD}$. A base model was initially selected that appropriately described the time course of aripiprazole plasma concentrations in Study 1 accounting for IM absorption of $AL_{NCD}$ and conversion to aripiprazole.

The initial base model was then expanded following the inclusion of final data from Study 3 (which was completed before Study 2) and used to re-estimate model parameters. Upon receipt of the final data from Study 2, the model was updated, existing parameters were re-estimated and full covariate analysis performed.

Covariates available for evaluation included the following: continuous covariates—age (yr) at baseline, and body weight (WT) (kg) at baseline and the categorical covariates—injection site (gluteal or deltoid) formulation, CYP2D6 genotype, ethnicity, gender, and race. Body weight, formulation and CYP2D6 genotype were evaluated as part of the initial base model development with Study 1. The covariate model was re-evaluated following receipt of the data from Study 3 and Study 2. The effects of body weight on clearance (CL) and volume (V) terms were incorporated using fixed allometric exponents of 0.75 and 1, respectively, and scaled to 70 kg (7). All relevant covariates were added to the model (the full model), and backward deletion was performed to assess the relative influence of each covariate on the model by deleting it from the full model on an individual basis until a final model was identified.

Subsequently, data from Study 4 were added (to include data from administration of AL alone) and the final model parameters were updated based on the data from all four studies. The model was evaluated using goodness-of-fit analyses and by generating prediction corrected visual predictive checks (pcVPCs).

Initial simulations for oral aripiprazole dosed at 15 mg for 21 days suggested that the final PopPK model may over-predict the exposure to aripiprazole with multiple oral doses. Investigations showed that the variability in aripiprazole concentrations associated with the 21-day oral regimen in Study 2 was high but consistent with what was previously observed in the pivotal phase 3 study and that there appeared to be a sub-group of individuals whose profiles reflected a lower exposure following multiple oral aripiprazole administration. A mixture model was evaluated for oral aripiprazole to see if a subpopulation could be formally identified.

The final PopPK model and mixture model for oral aripiprazole were used as appropriate to perform Monte Carlo simulations using Pharsight Trial Simulator version 2.2.2 (Certara USA, Inc, Princeton, NJ). In total, 500 individual concentration-time profiles were simulated for each scenario without incorporation of the residual error from the final PopPK model. Simulations were conducted:

To evaluate the impact on aripiprazole concentrations when the-1-day initiation regimen is co-administered with AL on the same day as compared to administering AL several days later. Simulations were conducted for all five approved AL dosage strengths and dose intervals (441, 662, and 882 mg q4w, 882 mg q6w, and 1064 mg q8w) with administration of the 1-day initiation regimen (a single dose of $AL_{NCD}$ and a single 30 mg dose of oral aripiprazole) on the same day. In addition, simulations were also carried out where AL (all approved doses) was administered 1, 3, 7, 10, or 14 days after the 1-day initiation regimen. AL treatment was continued at the prescribed dosing interval from the point of the first administration.

To evaluate the use of $AL_{NCD}$ as an alternative to the current recommendation of daily oral aripiprazole supplementation to re-establish therapeutic aripiprazole plasma concentrations following a missed dose of AL. 'Re-establishment' regimens ($AL_{NCD}$ or the 1-day initiation regimen) were begun at the same time as the late dose. Simulations were carried out to predict likely aripiprazole concentration-time profiles following multiple-dose scenarios to determine the likely impact of a late AL dose with and without supplementation with $AL_{NCD}$. Five AL dosing regimens were simulated (441, 662, and 882 mg q4wk, 882 mg q6wk, and 1064 mg q8wk) at steady state. A dose of AL was administered 1, 2, 3, 4, or 6 weeks late, either alone or supplemented with 7 days oral aripiprazole or $AL_{NCD}$.

The base model was parameterized to describe aripiprazole following single IM administration of $AL_{NCD}$, single IM administration of AL, and oral aripiprazole administration from Study 1, 2 and 3. The model contained central and peripheral compartments for aripiprazole and 16 structural parameters.

The previous PopPK model for aripiprazole following administration of AL and oral aripiprazole included covariate terms to describe an increase in VC/F with body weight (power model fixed at allometric exponent of 1.0) alongside a reduction in CL/F for CYP2D6 poor metabolizers. However, the current dataset did not contain any poor metabolizers; consequently, CYP2D6 phenotype was not evaluated for the current dataset. Based on the eta versus covariate plots, WT was tested on VC/F (power model fixed at allometric exponent of 1.0), CL/F, D and ALAG for AL. Additionally, the potential effects of age on CL/F, $AL_{NCD}$ injection site on FRAC, and AL injection site on D and ALAG. For injection site effects the change in parameter following administration in the deltoid was estimated with in the gluteal used as the reference. There were limited number of Hispanic or Latino patients (5%), thus ethnicity was not included in the covariate analysis. Race and gender were not included as there were no apparent differences in the model parameter estimates.

The base model was updated to include 8 covariate effects to form a full covariate model. Parameters associated with AL administration were consistent with prior analyses. Of the eight effects in the model, two of the estimated injection site effects included the null value ($AL_{NCD}$ injection site on FRAC and AL injection site on ALAG), and were removed. Removal of age on CL/F, VVT on ALAG, WT on input D, AL injection site on D, VVT on CL/F resulted in insignificant changes in the OFV. Thus, the model resulting from backward elimination contained just the single covariate effect of increasing VC/F with WT.

Data from Study 4 were added (to include data from AL administration alone) to develop the final PopPK model. A 2-compartment model with central and peripheral compartments for aripiprazole and conversion of IM AL to aripiprazole described by a zero-order process with the D of conversion estimated and the first-order absorption of aripiprazole from the dosing depot defined as 1/D1 was used. Additionally, ALAG from the IM AL depot to the appearance of aripiprazole in the central compartment was present. First-order processes described the absorption of aripiprazole following oral dosing, and the movement between central and peripheral compartments, all as per the previous model. However, the previous model was now updated to include a double Weibull function that described the conversion of IM $AL_{NCD}$ to aripiprazole in plasma following IM $AL_{NCD}$ administration.

Goodness-of-fit analyses demonstrated that the observed concentrations were well described by model predictions with no apparent study, administration route, or observed dose-effect biases. pcVPC plots were created by study and by regimen within Study 2 and Study 4. The pcVPCs indicated that within and across studies for Study 1 and Study 3, and by regimen within Study 2 and Study 4, the majority of observed concentrations were contained within the final PopPK model-predicted 90% PIs. The final PopPK model was deemed adequate to perform simulations evaluating various dosing and administration scenarios.

A mixture model was applied to patients receiving the 21-day initiation regimen in Study 2 to account for a subgroup of patients with lower exposure following multiple oral aripiprazole administration over the first 28 days of dosing. The mixture model estimated there to be a subpopulation of patients (37.4%; 95% CI 22.3% to 55.4%) in the 21-day initiation regimen groups in Study 2 that had 44.6% lower FPO (95% CI: 40.9-48.3%). These estimates of reduction n in FPO and proportion of patients in the subpopulation from the mixture model were applied to the final PopPK model in the formal simulations.

The observed results of Study 2 demonstrated that the co-administration of the 1-day initiation regimen with AL 441 mg and 882 mg achieves therapeutic concentrations of aripiprazole within 4 days, similar to the concentrations achieved with the 21-day initiation regimen administered in conjunction with the first AL dose (Hard et al. CNS Drugs, submitted; Aristada USPI, 2017). Simulations were conducted for all approved AL dosage strengths and dose intervals (441, 662, and 882 mg q4w, 882 mg q6w, and 1064 mg q8w) with the 1-day initiation regimen given the same day as the starting dose of AL. In all cases, same-day administration of AL and the 1-day initiation regimen was predicted to provide rapid and sustained levels of aripiprazole within 4 days of treatment initiation for all regimens. Aripiprazole concentrations remained comparable for all five AL doses over the first two weeks. Following the first two weeks, AL-dose related differences in aripiprazole concentrations start to become apparent as expected.

Simulations were conducted to evaluate whether the 1-day initiation regimen could be administered prior to, and on a separate day from the first dose of AL. As before all five AL dosing regimens were simulated (441, 662, and 882 mg q4wk, 882 mg q6wk, and 1064 mg q8wk). For all scenarios the 1-day initiation regimen was administered on Day 1, and the first AL dose was given on the same day as the 1-day initiation regimen or 1, 3, 7, 10, or 14 days following the 1-day initiation regimen (i.e., starting AL on Days 2, 4, 8, 11, and 15). AL was then continued at the prescribed dosing interval from that point forward.

Delaying the start of AL relative to the start of the 1-day initiation regimen reduced median aripiprazole concentrations over the first two dosing intervals of AL compared with simultaneous treatment initiation, and the magnitude of this effect was determined by the length of the delay. When AL was administered 1 or 3 days after the 1-day initiation regimen, negligible decreases in aripiprazole concentrations were observed at the end of the AL dosing interval (Ct) compared to when AL was administered on the same day as the 1-day initiation regimen. Delays in the first AL injection ≥1 week from the 1-day initiation regimen were also assessed. When AL was administered 7, 10, or 14 days later, the median CT was lower by 8% to 16%, 9% to 23%, and 14% to 31%, respectively, compared to same day administration as the 1-day initiation regimen. When the AL dose was administered 10 days following the 1-day initiation regimen CT was reduced by ≤23% compared to when both were administered on Day 1.

Simulations were performed to evaluate the use of $AL_{NCD}$ as an alternative to the current recommendations to use 7 days oral supplementation following a missed AL injection. All approved AL dosing regimens were simulated (441, 662, and 882 mg q4wk, 882 mg q6wk, and 1064 mg q8wk) at steady state. A dose of AL was administered 1, 2, 3, 4, or 6 weeks late (depending on the dosing regimen) either alone, with 7 days of supplemental oral aripiprazole or with a single injection $AL_N$co (without the single oral aripiprazole dose).

Median simulated aripiprazole concentrations for selected late dosing scenarios for the five approved AL regimens (with and without the re-establishment regimens) currently require 7 days oral aripiprazole supplementation with the late dose in order to restore therapeutic aripiprazole concentrations (Aristada US PI 2017). In these simulations, late administration of the AL dose resulted in expectedly lower median predicted concentrations after the late dose than when the AL dose was not delayed. When $AL_{NCD}$ was used in conjunction with AL following a missed dose, aripiprazole concentrations rose and reached $C_{max}$ values that were similar to those achieved with 7 days of oral aripiprazole and span the maximal concentration range associated with the approved dose range of AL.

When an AL dose was not missed, aripiprazole $C_{max}$ ranged from 153 to 310 ng/mL. Both re-establishment regimens resulted in $C_{max}$ values within a comparable range to $C_{max}$ values for AL at steady-state, and thus were adequate at returning concentrations to therapeutic levels. These simulations demonstrate that when an AL dose is missed, either 7 days of oral aripiprazole or $AL_{NCD}$ can be used to return aripiprazole concentrations to the therapeutic range.

Therefore, $AL_{NCD}$ is a suitable alternative to daily oral aripiprazole supplementation for recovery of aripiprazole concentrations following a missed AL dose. Further simulations indicated that longer delays (requiring 21 days of oral aripiprazole supplementation according to the current prescribing information [Aristada PI, 2017]) would require resumption of AL treatment with the $AL_{NCD}$ and 30 mg oral aripiprazole combination.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating schizophrenia in a subject in need thereof, the method comprising administering to the subject:
   a first component comprising about 5-50 mg of aripiprazole;
   a second component comprising about 629-695 mg of $AL_{NCD}$ having a volume-based particle distribution size (Dv50) between about 175 nm and about 350 nm; and
   a third component comprising a therapeutically effective amount of aripiprazole lauroxil;
   wherein the method comprises a regimen wherein the first component is only administered on the first and/or second days of treatment, the second component is only administered on the first day of treatment, and the third component is only administered once within the first 10 days of treatment.

2. The method of claim 1, wherein the $AL_{NCD}$ comprises polysorbate 20, sodium citrate, sodium chloride, an aqueous buffer, and a population of particles of aripiprazole lauroxil, wherein the $AL_{NCD}$ has a ratio of particles to polysorbate 20 of between about 0.1:1 and about 40:1.

3. The method of claim 1, wherein the first component is administered at a dosage of about 30 mg or about 15 mg.

4. The method of claim 1, wherein the second component is administered at a dosage of about 675 mg of $AL_{NCD}$.

5. The method of claim 1, wherein the third component is administered at a dosage of about 300-1500 mg.

6. The method of claim 1, wherein the third component is administered at a dosage of 441, 662, 882, or 1064 mg.

7. The method of claim 1, wherein the method comprises a regimen wherein the first, second, and third components are administered at substantially the same time, followed by a second treatment comprising administering the third component alone.

8. The method of claim 7, wherein the second treatment occurs no earlier than 21 days after the initial treatment.

9. The method of claim 1, wherein the first component is only administered once during the treatment duration.

10. The method of claim 1, wherein the first component is not administered again within 21 days following the initial treatment.

11. The method of claim 9, wherein the third component is administered on the first or second day of treatment.

12. The method of claim 9, wherein the third component is administered 7-10 days after the start of the treatment regimen.

13. The method of claim 9, wherein the first component is only administered on the first day of treatment.

14. The method of claim 1, wherein the first component is administered orally.

15. The method of claim 1, wherein the second component and third component are administered intra-muscularly to the deltoid or gluteus.

16. A method of treating schizophrenia in a subject in need thereof, the method comprising administering to the subject:
   a first component comprising aripiprazole;
   a second component comprising $AL_{NCD}$ having a volume-based particle distribution size (Dv50) between about 175 nm and about 350 nm; and
   a third component comprising aripiprazole lauroxil;
   wherein the dosages of the first, second, and third components combined are sufficient to maintain a therapeutically effective mean blood plasma level of aripiprazole in the subject; and
   wherein the method comprises a regimen wherein the first component is only administered on the first and/or second days of treatment, the second component is only administered on the first day of treatment, and the third component is only administered once within the first 10 days of treatment.

17. The method of claim 16, wherein the $AL_{NCD}$ comprises polysorbate 20, sodium citrate, sodium chloride, an aqueous buffer, and a population of particles of aripiprazole lauroxil, wherein the $AL_{NCD}$ has a ratio of particles to polysorbate 20 of between about 0.1:1 and about 40:1.

18. The method of claim 16, wherein the therapeutically effective mean blood plasma level of aripiprazole is reached within 24 hours of the initial treatment.

19. The method of claim 16, wherein the therapeutically effective mean blood plasma level of aripiprazole is maintained for no less than 21 days.

20. The method of claim 16, wherein the first component is only administered once during the treatment duration.

21. The method of claim 16, wherein the first component is not administered again within 21 days following the initial treatment.

22. The method of claim 16, wherein the regimen further comprises a second administration of the third component alone.

23. The method of claim 16, wherein the third component is administered on the first or second day of treatment.

24. The method of claim 16, wherein the third component is administered 7-10 days after the start of the treatment regimen.

25. The method of claim 16, wherein the first component is only administered on the first day of treatment.

26. The method of claim 16, wherein the first component is administered orally.

27. The method of claim 16, wherein the second component and third component are administered intra-muscularly to the deltoid or gluteus.

* * * * *